US011090308B2

(12) United States Patent
Taub

(10) Patent No.: US 11,090,308 B2
(45) Date of Patent: Aug. 17, 2021

(54) METHODS OF TREATING LIVER DISORDERS OR LIPID DISORDERS WITH A THR-BETA AGONIST

(71) Applicant: Madrigal Pharmaceuticals, Inc., West Conshohocken, PA (US)

(72) Inventor: Rebecca Taub, Villanova, PA (US)

(73) Assignee: Madrigal Pharmaceuticals, Inc., West Conshohocken, PA (US)

( * ) Notice: Subject to any disclaimer, the term of this patent is extended or adjusted under 35 U.S.C. 154(b) by 0 days.

(21) Appl. No.: 16/343,065

(22) PCT Filed: Oct. 18, 2017

(86) PCT No.: PCT/US2017/057203
§ 371 (c)(1),
(2) Date: Apr. 18, 2019

(87) PCT Pub. No.: WO2018/075650
PCT Pub. Date: Apr. 26, 2018

(65) Prior Publication Data
US 2020/0230146 A1    Jul. 23, 2020

Related U.S. Application Data

(60) Provisional application No. 62/516,594, filed on Jun. 7, 2017, provisional application No. 62/409,833, filed on Oct. 18, 2016.

(51) Int. Cl.
*A61K 31/53* (2006.01)
*A61P 1/16* (2006.01)
*A61P 3/06* (2006.01)

(52) U.S. Cl.
CPC .............. *A61K 31/53* (2013.01); *A61P 1/16* (2018.01); *A61P 3/06* (2018.01)

(58) Field of Classification Search
CPC ........ A61K 31/53; A61K 31/50; A61K 31/501; C07D 403/12; C07D 237/16;
(Continued)

(56) References Cited

U.S. PATENT DOCUMENTS 7,452,882 B2    11/2008   Hayes et al.
7,807,647 B2    10/2010   Sheikhnejad et al.
(Continued)

FOREIGN PATENT DOCUMENTS

CN        101014608 A     8/2007
CN        101228135 A     7/2008
(Continued)

OTHER PUBLICATIONS

Harrison et al. (Powerpoint slides from Madrigal Pharmaceuticals, 2013-2015).*

(Continued)

*Primary Examiner* — Savitha M Rao
(74) *Attorney, Agent, or Firm* — Cooley LLP; Heidi A. Erlacher; Chun Liang Yu

(57) ABSTRACT

The present invention provides a method for treating a liver disorder or lipid disorder in a subject in need thereof with 2-(3,5-dichloro-4-((5-isopropyl-6-oxo-1,6-dihydropyridazin-3-yl)oxy)phenyl)-3,5-dioxo-2,3,4,5-tetrahydro-1,2,4-triazine-6-carbonitrile, a stereoisomer, a salt thereof, or a morphic form thereof.

11 Claims, 4 Drawing Sheets

$^{14}$C-MGL-3196 In Rats

(58) Field of Classification Search
CPC ....... C07D 237/14; C07D 403/02; A61P 5/14; A61P 9/00; Y02P 20/55
See application file for complete search history.

(56) References Cited

U.S. PATENT DOCUMENTS

| | | | |
|---|---|---|---|
| 7,807,674 | B2 | 10/2010 | Hayes et al. |
| 8,076,334 | B2 | 12/2011 | Hayes et al. |
| 9,266,861 | B2 | 2/2016 | Hester et al. |
| 9,968,612 | B2 | 5/2018 | Taub et al. |
| 10,376,517 | B2 | 8/2019 | Taub et al. |
| 2009/0082310 | A1 | 3/2009 | Haynes et al. |
| 2019/0381053 | A1 | 12/2019 | Taub et al. |

FOREIGN PATENT DOCUMENTS

| | | |
|---|---|---|
| CN | 101801960 A | 8/2010 |
| EA | 200901651 | 12/2010 |
| JP | S5615272 A | 2/1981 |
| JP | 2009501759 A | 1/2009 |
| RU | 2379295 | 1/2010 |
| TW | 200745052 | 12/2007 |
| WO | WO 2005/118824 A2 | 12/2005 |
| WO | WO 2007/009913 A1 | 1/2007 |
| WO | WO 2008/149379 A2 | 12/2008 |
| WO | WO-2009/037172 A1 | 3/2009 |
| WO | WO-2014/043706 A1 | 3/2014 |

OTHER PUBLICATIONS

Rodríguez-Spong B. et al. , "General principles of pharmaceutical solid polymorphism: a supramolecular perspective", Adv Drug Deliv Rev.;56(3):241-274 (2004).
Beliard, S. et al. "Improvement in LDL-cholesterol levels of patients with familial hypercholesterolemia: can we do better? Analysis of results obtained during the past two decades in 1669 French subjects", Atherosclerosis. May 2014;234(1):136-41.
Kelly, M. J. et al. "Discovery of 2-[3,5-dichloro-4-(5-isopropyl-6-oxo-1,6-dihydropyridazin-3-yloxy)phenyl]-3,5-dioxo-2,3,4,5-tetrahydro[1,2,4]triazine-6-carbonitrile (MGL-3196), a Highly Selective Thyroid Hormone Receptor β agonist in clinical trials for the treatment of dyslipidemia", J Med Chem. May 22, 2014;57(10):3912-23.
Nigam, S. K. et al. "What do drug transporters really do?" Nat Rev Drug Discov. Jan. 2015;14(1):29-44.
Nordestgaard, B. G. et al., "Familial hypercholesterolaemia is underdiagnosed and undertreated in the general population: guidance for clinicians to prevent coronary heart disease: Consensus Statement of the European Atherosclerosis Society", Eur Heart J. Dec. 2013;34(45):3478-90.
Pinto, N. et al. "Clinically relevant genetic variations in drug metabolizing enzymes", Curr Drug Metab. Jun. 2011;12(5):487-97.
Taub R. et al. "Lipid lowering in healthy volunteers treated with multiple doses of MGL-3196, a liver-targeted thyroid hormone receptor-β agonist", Atherosclerosis. Oct. 2013;230(2):373-80.
Abel, E. D. et. al., "Divergent roles for thyroid hormone receptor β isoforms in the endocrine axis and auditory system", J. Clin. Invest; 104(3):291-300 (Aug. 1999).
Adams, M. et al., "Genetic Analysis of 29 Kindreds with Generalized and Pituitary Resistance to Thyroid Hormone: Identification of Thirteen Novel Mutations in the Thyroid Hormone Receptor β Gene," J. Clin. Invest; 94:506-515 (1994).
Ashizawa, K., "Physico-Chemical Studies on the Molecular Details of Drug Crystals", Pharm Tech Japan; 18(10):81-96 (Sep. 2002).
Byrn, S. et al., "Pharmaceutical Solids: A Strategic Approach to Regulatory Considerations", Pharmaceutical Research; 12(7): 945-954 (1995).
Caira, M. R., "Crystalline Polymorphism of Organic Compounds", Topics in Current Chemistry, 198:163-208 (1998).

Charushin, V. et al. "Six-membered Rings with Three or more Heteroatoms, and their Fused Carbocyclic Derivatives: 1,2,4-Triazines and their Benzo Derivatives", 9.02, Comprehensive Heterocyclic Chemistry III (2008).
Gloss, B. et. al. "Cardiac Ion Channel Expression and Contractile Function in Mice with Deletion of Thyroid Hormone Receptor α or β", Endocrinology, 142(2): 544-550 (2001).
Goldfuss, B., "Organolithiums in Enantioselective Additions to π* and σ* Carbon-Oxygen Electrophiles", Synthesis, (14): 2271-2280 (2005).
Hara, Y., et al. "Thyroid hormone resistance", Japanese Journal of Clinical Medicine, Syndrome by Region Series (1) Endocrine Syndrome (First volume): 254-257 (1993).
Hickey, D. M. B. et al., "Synthesis of Thyroid Hormone Analogues. Part 3. Iodonium Salt Approaches to SK&F L-94901", J. Chem. Soc.: 3103-3111 (1988), Abstract.
Hilfiker, R. et al. "Relevance of Solid-State Properties for Pharmaceutical Products", Polymorphism in the Pharmaceutical Industry, Wiley-VCH: 1-19 (Jan. 2006).
Huber, B. R. et al. "Two Resistance to Thyroid Hormone Mutants with Impaired Hormone Binding", Molecular Endocrinology, 17(4): 643-652 (Apr. 2003).
Huber, B. R. et al., "Thyroid Hormone Receptor-β Mutations Conferring Hormone Resistance and Reduced Corepressor Release Exhibit Decreased Stability in the N-Terminal Ligand-Binding Domain", Molecular Endocrinology, 17(1): 107-116 (2003).
Johansson, C. et. al., "Evidence that decreased heart rate in thyroid hormone receptor-α1-deficient mice is an intrinsic defect", Am. J. Physiol., 275: R640-R646 (1998).
Johatapurkar, A. A. et al., "Selective Thyromimetics Using Receptor and Tissue Selectivity Approaches: Prospects for Dyslipidemia", J. Med. Chem. 55(12): 5649-5675 (2012).
Kawaguchi, Y. et al., "Drug and crystal polymorphism", Journal of Human Environmental Engineering, 4(2): 310-317 (2002).
Kumar, S. et al., "Pharmaceutical Solid Dispersion Technology: A Strategy to Improve Dissolution of Poorly Water-Soluble Drugs", Recent Patents on Drug Delivery & Formulation, 7(2):111-121 (May 2013).
Lazar, M. A., "Thyroid Hormone Receptors: Multiple Forms, Multiple Possibilities", Endocrine Reviews, 14(2): 184-193 (1993).
Lu, C. et al., "Steroids: Extranuclear signaling of mutated thyroid hormone receptors in promoting metastatic spread in thyroid carcinogenesis", Steroids, 76(9):885-91 (2001).
Office Action dated Jun. 27, 2017 for Japanese Patent Application No. JP2015-532148: 10 pages.
Office Action dated Sep. 10, 2019 for Japanese Patent Application No. JP2018-217045: 9 pages.
Ooshima, H., "Crystallization of Polymorphs and Pseudo-polymorphs and Its Control," Pharm Stage, 6(10): 48-53 (2007).
Refetoff, S., "The Syndromes of Resistance to Thyroid Hormone", Endocrine Reviews, 14(3): 348-399 (Jun. 1993).
Riyuuzou, N. et al. "Insecticidal N-benzoyl-N'-phenylureas", CAPLUS Abstract CA 94:208901 for JP-S5615272-A (Feb. 14, 1981).
Serajuddin, A. T., "Solid Dispersion of Poorly Water-Soluble Drugs: Early Promises, Subsequent Problems, and Recent Breakthroughs", J Pharm Sci.; 88(10):1058-66 (Oct. 1999).
Shi, Y. et al., "Mutant-Selective Thyromimetics for the Chemical Rescue of Thyroid Hormone Receptor Mutants Associated with Resistance to Thyroid Hormone", Biochemistry 44: 4612-4626 (2005).
Stahly, G. P. et al., "Diversity in Single- and Multiple-Component Crystals. The Search for and Prevalence of Polymorphs and Cocrystals". Crystal Growth & Design, 7(6): 1007-1026 (2007).
Swain, C. G. et al., "The Mechanism of Addition of Grignard Reagents to Ketones", J. Am. Chem. Soc.; 73(2):870-872 (1951).
Takata, N. "API form screening and selection in drug discovery stage", Pharm Stage, 6(10): 20-25 (2007).
"Test Procedures and Acceptance Criteria for New Drug Substances and New Drug Products", PMSB/ELD Notification (568): 45 pages (2001).
Wagner R. L. et al., "Hormone Selectivity in Thyroid Hormone Receptors", Molecular Endocrinology, 15(3): 398-410 (2001).

(56) References Cited

OTHER PUBLICATIONS

Weiss R. E. et al. "Resistance to Thyroid Hormone (RTH) in the Absence of Abnormal Thyroid Hormone Receptor (TR) (nonTR-RTH)," Hot Thyroidology Sep. 2009: 11 pages (2009).
Yamada, M., "Resistance to thyroid hormone", Nihon Rinsho, 64(12): 2237-42 (Dec. 2006).
Yamano, M., "Approach to Crystal Polymorph in Process Research of New Drug", Journal of Synthetic Organic Chemistry, 65(9): 907-913 (2007).
Ye, H. F. et al., "A Subtype-Selective Thyromimetic Designed to Bind a Mutant Thyroid Hormone Receptor Implicated in Resistance to Thyroid Hormone", J Am Chem Soc, 123(7):1521-2 (Feb. 21, 2001).
Yen, P. M., "Physiological and Molecular Basis of Thyroid Hormone Action", Physiological Reviews, 81(3): 1097-1142 (2001).
Ashby, E. C. et al., "Mechanisms of Grignard reagent addition to ketones", Acc. Chem. Res.; 7:272-280. (1974).
Harrison, S.A. et al. "Resmetirom (MGL-3196) for the treatment of non-alcoholic steatohepatitis: a multicentre, randomised, double-blind, placebo-controlled, phase 2 trial." Lancet. Nov. 30, 2019;394(10213):2012-2024. doi: 10.1016/S0140-6736(19)32517-6.

\* cited by examiner

METHODS OF TREATING LIVER DISORDERS OR LIPID DISORDERS WITH A THR-BETA AGONIST

RELATED APPLICATIONS

This application is a U.S. National Phase application, filed under 35 U.S.C. § 371, of International Application No. PCT/US2017/057203, filed on Oct. 18, 2017, which claims priority to and the benefit of U.S. Ser. No. 62/409,833, filed on Oct. 18, 2016, and U.S. Ser. No. 62/516,594, filed on Jun. 7, 2017, the contents of each of which are incorporated herein by reference in their entireties.

BACKGROUND

Non-alcoholic steatohepatitis (NASH) is the most common chronic liver disease in the United States. NASH is a fatty inflammation of the liver and a major cause of cirrhosis, fibrosis and liver failure. The disease is progressive, starting as steatosis or nonalcoholic fatty liver disease (NAFLD), progressing to an inflamed fatty liver (NASH), and eventually leading to cirrhosis and fibrosis. The disease is generally asymptomatic until severe liver impairment occurs.

The prevalence of NAFLD in the U.S. population is about 20-23%, and may be as high as 33%, and the prevalence of NASH in the U.S. population is about 2-3%. Some NASH patients will progress to late stage disease: approximately 15-50% of NASH patients progress to severe fibrosis, and approximately 7-16% progress to cirrhosis. The rate of liver-specific mortality in NASH cirrhotics is approximately 10% per decade.

Currently, no specific therapies for NASH exist.

Despite advances in treatment, approximately 70% of high-risk cardiovascular (CV) patients do not achieve low-density lipoprotein cholesterol (LDL-C) goals, and as many as 10% of hypercholesterolemic patients do not tolerate statins. Elevated LDL-C levels are associated with CV disease, including myocardial infarctions and strokes, and drugs such as statins that lower LDL-C and also reduce CV morbidity and mortality.

Familial hypercholesterolaemia is underdiagnosed and undertreated in the general population (See, e.g., B. G. Nordestgaard, et al., European Heart Journal, 2013, 34, 3478-3490). Heterozygous familial hypercholesterolemia (HeFH) and homozygous familial hypercholesterolemia (HoFH) are genetic disorders characterized by severe debilitating dyslipidemia and early onset CV disease. Individuals with HeFH typically have LDL-C levels approximately double that of unaffected siblings. HeFH is most commonly caused by mutations of the low-density lipoprotein receptor (LDLR) gene. If untreated, early onset coronary artery disease will likely develop in HeFH patients. The prevalence of HeFH is estimated to be 1 in 500 and may be as high as 1 in 200. Despite treatment with newer therapies (e.g., proprotein convertase subtilisin/kexin type 9 [PCSK9] inhibitors) and standard care (which includes statins and ezetimibe), some HeFH patients are not achieving their LDL-C goal. A recent retrospective study of HeFH patients followed over two decades revealed that only 18.8% of the patients receiving maximal therapy (i.e., statins with a potency of >45% LDL-C reduction plus at least another lipid-lowering agent) reach target LDL-C levels of <100 mg/dL (See, e.g., Atherosclerosis, 2014 May, 234(1):136-41).

SUMMARY

The present disclosure provides a method of treating a liver disorder or lipid disorder in a subject in need thereof, the method comprising: (a) administering a first dose of 2-(3,5-dichloro-4-((5-isopropyl-6-oxo-1,6-dihydropyridazin-3-yl)oxy)phenyl)-3,5-dioxo-2,3,4,5-tetrahydro-1,2,4-triazine-6-carbonitrile ("Compound A") to the subject daily for a first period of time; (b) performing a test selected from the group consisting of a genetic test, a biomarker test, and a pharmacokinetic test on a biological sample obtained from the subject, a physical examination of the subject, and a combination thereof, to determine sensitivity of the subject to Compound A after step (a); and (c) administering a second dose of Compound A to the subject for a second period of time based on the sensitivity result from step (b). In one embodiment, the test of step (b) is a biomarker test measuring the expression level of at least one biomarker. In one embodiment, the method further comprises (d) performing a first biomarker test on a first biological sample obtained from the subject before step (a), wherein the first biomarker test measures the expression level of at least one biomarker that is to be measured in step (b); and (e) determining a change or degree of change in the expression level of the at least one biomarker based on the results in steps (b) and (d). In one embodiment, the method further comprises step (f) determining the second dose of Compound A based on the change or degree of change determined in step (e). In one embodiment, the determining the second dose of Compound A in step (f) is further based on at least one demographic feature of the subject, medication history of the subject, physical information of the subject, or a combination thereof.

The present disclosure also provides a method of treating a liver disorder or lipid disorder in a subject in need thereof, the method comprising: (a) performing a test selected from the group consisting of a genetic test, a biomarker test, and a pharmacokinetic test on a biological sample obtained from the subject, a physical examination of the subject, and a combination thereof; (b) determining a therapeutically effective amount of Compound A for the subject based on the result of the test; and (c) administering the therapeutically effective amount of Compound A to the subject. In one embodiment, a predictive algorithm is used in step (b) to determine the therapeutically effective amount of Compound A.

In one embodiment, the determination of the therapeutically effective amount of Compound A in step (b) is further based on at least one demographic feature of the subject, medication history of the subject, physical information of the subject, or a combination thereof.

In one embodiment, the liver disorder is NASH.

In one embodiment, the lipid disorder is hyperlipidemia or hypercholesterolemia.

In one embodiment, the genetic test comprises detecting polymorphism in a polynucleotide encoding a drug transporter, a drug metabolizing enzyme, or a thyroid axis hormone, a thyroid pathway gene, a lipid pathway gene, or a combination thereof. For example, the drug transporter can be a solute carrier transporter or an ATP-binding cassette transporter. For example, the ATP-binding cassette transporter can be selected from the group consisting of ABCC1, ABCC2, ABCC3, ABCC4, ABCC5, ABCG2, and ABCB11. For example, the solute carrier transporter can be selected from the group consisting of SLC22A1, SLC22A2, SLC22A3, SLC22A6, SLC22A8, SLC22A11, SLCO1B1, SLCO1B3, SLCO2B1, SLC47A1, and SLC47A2. In some embodiments, the drug metabolizing enzyme is CYP2C8.

In one embodiment, the biomarker test comprises measuring the expression level of a biomarker selected from the group consisting of thyroid axis hormones, thyroxine-binding globulin (TBG), sex hormone-binding globulin (SHBG), and a lipid biomarker. For example, the thyroid axis hormone can be triiodothyronine (free T3) or a metabolite thereof, reverse T3 or a metabolite thereof, free thyroxine (T4) or a metabolite thereof, thyrotropin (TSH) or a metabolite thereof, a thyrotropin-releasing hormone (TRH) or a metabolite thereof, or a combination thereof. For example, the lipid biomarker can be selected from the group consisting of total cholesterol, triglycerides, low-density lipoprotein cholesterol (LDL-C), high-density lipoprotein cholesterol (HDL-C), non-HDL-C, lipoprotein(a), apolipoprotein A1 (ApoA-1), apolipoprotein B (ApoB), and a combination thereof.

In one embodiment, the biological sample is a blood or serum sample.

In one embodiment, the first dose is in the range of about 5 to 300 mg (e.g., about 40 mg, about 50 mg, about 80 mg, about 100 mg, about 120 mg, about 140 mg, about 160 mg, about 180 mg, or about 200 mg).

In one embodiment, the second dose is in the range of about 5 to 300 mg (e.g., about 40 mg, about 50 mg, about 80 mg, about 100 mg, about 120 mg, about 140 mg, about 160 mg, about 180 mg, or about 200 mg). For example, the second dose is administered in the range of about 5 to 300 mg (e.g., about 40 mg, about 50 mg, about 80 mg, about 100 mg, about 120 mg, about 140 mg, about 160 mg, about 180 mg, or about 200 mg) daily.

In one embodiment, the effective amount is in the range of about 5 to 300 mg (e.g., about 40 mg, about 50 mg, about 80 mg, about 100 mg, about 120 mg, about 140 mg, about 160 mg, about 180 mg, or about 200 mg). For example, the effective amount is administered in the range of about 5 to 300 mg (e.g., about 40 mg, about 50 mg, about 80 mg, about 100 mg, about 120 mg, about 140 mg, about 160 mg, about 180 mg, or about 200 mg) daily.

In one embodiment, the second dose is lower than the first dose.

In one embodiment, the second dose is the same as the first dose.

In one embodiment, the second dose is higher than the first dose.

In one embodiment, Compound A is in a crystalline form, e.g., in a morphic form characterized by an X-ray powder diffraction pattern including peaks at about 10.5, 18.7, 22.9, 23.6, and 24.7 degrees 2θ.

In one embodiment, the first period of time is in the range of 2-21 days (e.g., about 1 week, about 2 weeks, or about 3 weeks).

In one embodiment, Compound A is formulated in a gel, tablet, pill, or capsule.

In one embodiment, Compound A is administered orally.

In one embodiment, Compound A is administered daily, e.g., once a day, twice a day, or three times a day.

In one embodiment, the subject is administered or has been administered at least one other therapeutic agent.

In one embodiment, the at least one other therapeutic agent is a statin.

In one embodiment, the pharmacokinetic test comprises measuring a level of a metabolite of Compound A in the biological sample at a predetermined time after the administration of the first dose. For example, the predetermined time can be at least 20 minutes.

In one embodiment, the metabolite of Compound A comprises a compound having the following structure:

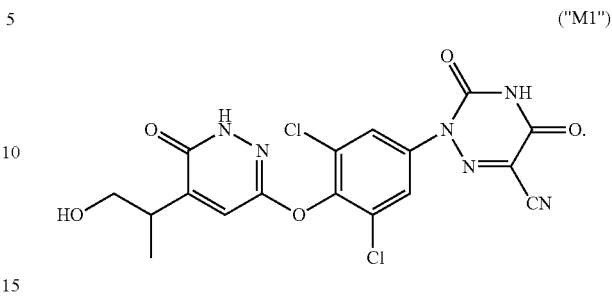

("M1")

In one embodiment, the metabolite has a geometric mean of maximum plasma concentration of about 100 ng/mL to 1000 ng/mL, e.g., about 150 ng/mL to 800 ng/mL.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

Other features and advantages of the disclosure will be apparent from the following detailed description and claims.

DETAILED DESCRIPTION OF THE DISCLOSURE

Figure 1:
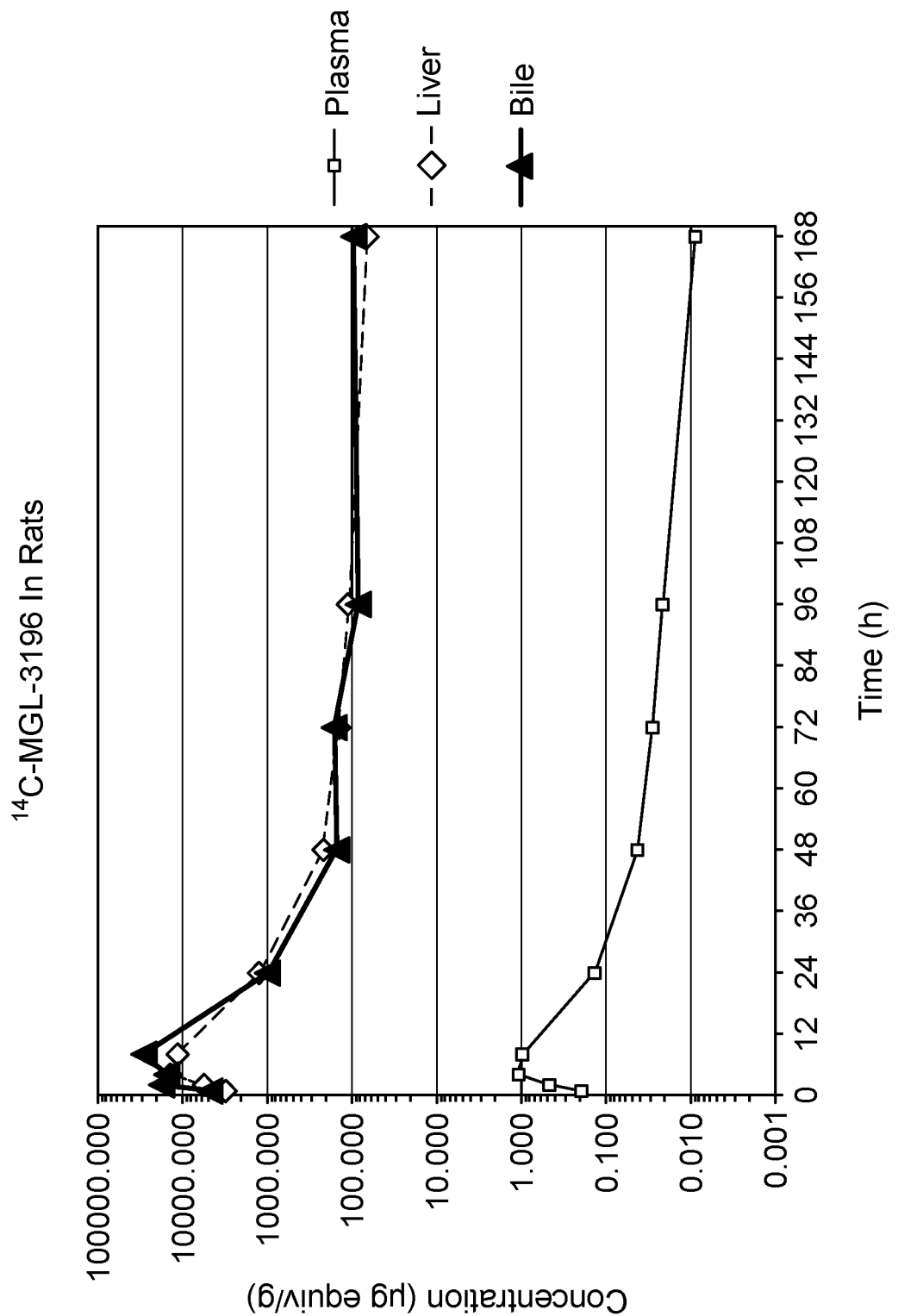
FIG. 1 is the concentration-time profile of [$^{14}$C]-MGL-3196 in liver, bile, and plasma showing high liver uptake (compared to plasma) and excretion into bile in rats.
Figure 2A:
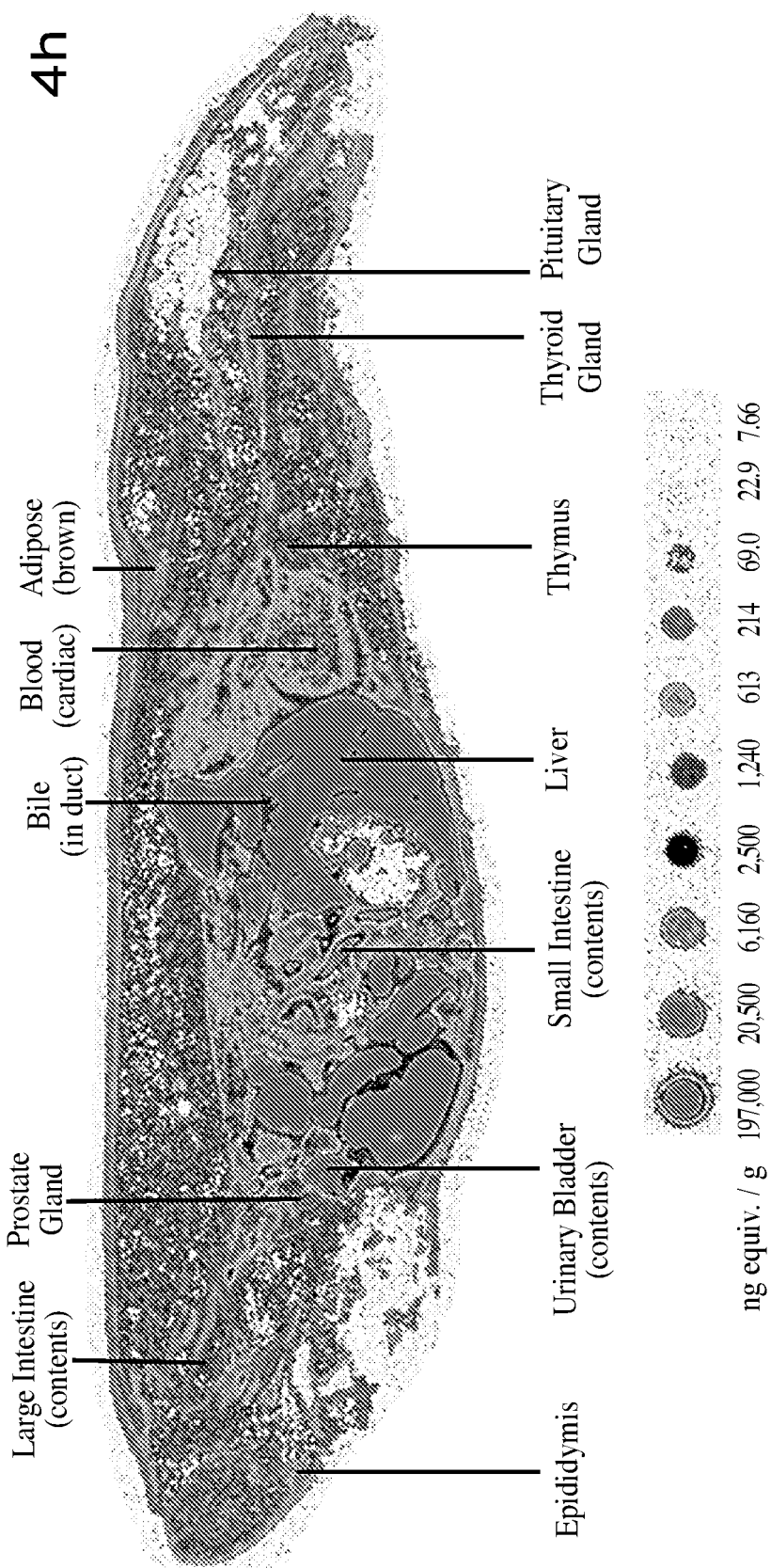
FIGS. 2A-2B are quantitative whole-body autoradiographs showing tissue distribution of [$^{14}$C]-MGL-3196 in rats at 4 h (FIG. 2A) and 24 h (FIG. 2B) after a single oral dose at 5 mg/kg. Autoradiographs show selective uptake of MGL-3186 into liver.
Figure 2B:
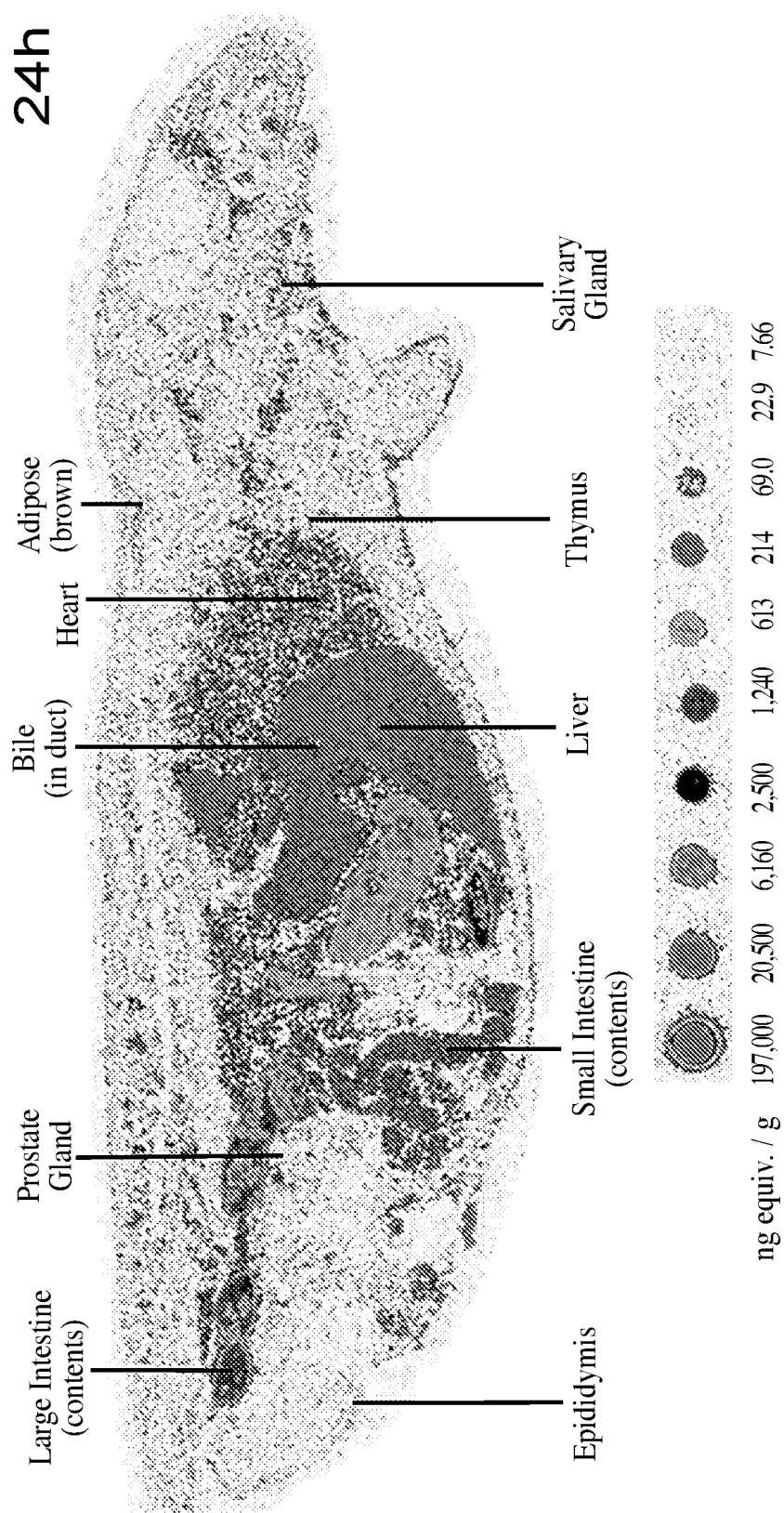
Figure 3:
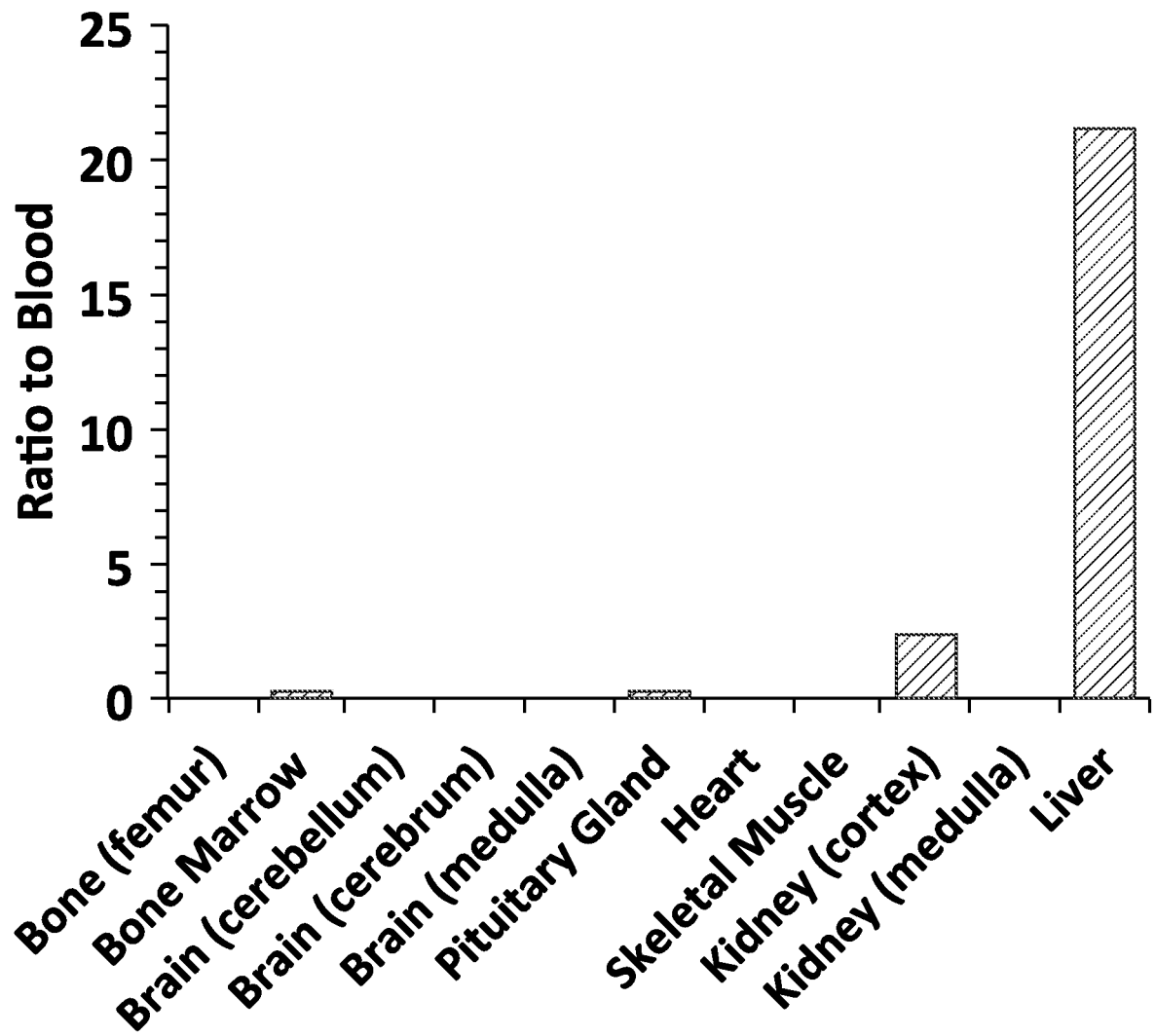
FIG. 3 is a graph of tissue to blood concentration ratios demonstrating selective uptake of MGL-3196 into liver and kidney. Remaining organs/tissues have ratios indicating that MGL-3196 is limited to the blood vasculature of those organs/tissues.

As used herein, the term "thyroid pathway gene" refers to any gene that encodes a protein involved in the thyroid pathway. Examples of thyroid pathway genes include DIO1 and DIO2.

As used herein, the term "lipid pathway gene" refers to any gene that encodes a protein involved in the lipid pathway. Examples of lipid pathway genes include MYLIP, ISC1, and a gene encoding HMG-CoA reductase.

As used herein, the term "sensitivity", when used in reference to a drug, refers to how well a subject responds to a drug. The present disclosure recognizes that one subject's sensitivity level to a drug can differ from another subject's sensitivity to the same drug. The sensitivity level can be determined by a genetic test, a biomarker test, a pharmacokinetic test, a physical examination, or a combination thereof, such as those described herein. For example, the genetic test can identify specific genetic profiles that can be used to stratify a patient population with respect to drug sensitivity. For example, after a first dose of Compound A is administered to a subject for a period of time, a pharmacokinetic test can be performed on the subject to measure drug exposure level, an indicator of drug sensitivity. If the drug exposure level is higher than an average drug exposure level, the subject is more sensitive to Compound A than the average patient population. A second dose of Compound A administered to the subject can be lower than the first dose.

As used herein, the term "sensitivity", when used in reference to a test (e.g., a genetic test, a biomarker test, a pharmacokinetic test, or a physical examination of the present disclosure), refers to the ability of the test to detect a difference of the same matter of interest in two or more samples when the difference is truly present. For example, the difference can be a difference in biomarker concentration.

As used herein, the term "specificity", when used in reference to a test (e.g., a genetic test, a biomarker test, a pharmacokinetic test, or a physical examination of the present disclosure), refers to the probability of the test to detect a matter of interest when it is truly present. For example, the matter of interest can be a biomarker or polymorphism in a drug transporter or drug metabolizing enzyme.

As used herein, "pharmaceutically acceptable excipient or carrier" means an excipient or carrier that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient. Suitable carriers are described in the most recent edition of Remington's Pharmaceutical Sciences, a standard reference text in the field.

As used herein, a "subject" can be any mammal, e.g., a human, a non-human primate, mouse, rat, dog, cat, cow, horse, pig, sheep, goat, camel. In a preferred embodiment, the subject is a human.

As used herein, a "subject in need thereof" is a subject having a liver disorder or lipid disorder, or a subject having an increased risk of developing a liver disorder or lipid disorder relative to the population at large. In one embodiment, a subject in need thereof has NASH. In another embodiment, a subject in need thereof has hyperlipidemia or hypercholesterolemia. In another embodiment, a subject in need thereof is being administered or has been administered a drug different from Compound A, for treating or preventing a liver disorder or lipid disorder. For example, a subject in need thereof is being administered or has been administered atorvastatin.

As used herein, "treating" describes the management and care of a patient for the purpose of combating a disease, condition, or disorder and includes decreasing or alleviating the symptoms or complications, or eliminating the disease, condition or disorder.

As used herein, "preventing" describes stopping the onset of the symptoms or complications of the disease, condition or disorder.

As used herein, the term "salt" is a pharmaceutically acceptable salt and can include acid addition salts including hydrochlorides, hydrobromides, phosphates, sulphates, hydrogen sulphates, alkyl sulphonates, arylsulphonates, acetates, benzoates, citrates, maleates, fumarates, succinates, lactates, and tartrates. A salt can also be formed between a cation and a negatively charged group on Compound A. Suitable cations include sodium ion, potassium ion, magnesium ion, calcium ion, and an ammonium cation such as tetramethylammonium ion. Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. A salt can also contain a quaternary nitrogen atom.

As used herein, "solvate" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$. A hydrate refers to, for example, a mono-hydrate, a di-hydrate, a tri-hydrate, etc.

The term "therapeutically effective amount," as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In one embodiment, the disease or condition to be treated is NASH. In another embodiment, the disease or condition to be treated is a lipid disorder.

The term "single nucleotide polymorphism (SNP)," as used herein, the term "single nucleotide polymorphism" or "SNP" refers to a particular base position in the genome where alternative bases are known to distinguish one allele from another. In some embodiments, one or a few SNPs and/or CNPs is/are sufficient to distinguish complex genetic variants from one another so that, for analytical purposes, one or a set of SNPs and/or CNPs may be considered to be characteristic of a particular variant, trait, animal, line, breed, cross-breed, or set thereof. In some embodiments, one or a set of SNPs and/or CNPs may be considered to define a particular variant, trait, animal, line, breed, cross-breed, or set thereof.

The term "biological sample," as used herein, refers to a sample obtained or derived from a biological source (e.g., a tissue or organism or cell culture) of interest, as described herein. In some embodiments, a source of interest comprises or consists of an organism, such as an animal or human. In some embodiments, a biological sample comprises or consists of biological tissue or fluid. In some embodiments, a biological sample may be or comprise bone marrow; blood; blood cells; serum; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; tissue biopsy specimens; surgical specimens; other body fluids, secretions, and/or excretions; and/or cells therefrom, etc. In some embodiments, a biological sample comprises or consists of cells obtained from an individual. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc. The term "about", "approximately", or "approximate", when used in connection with a numerical value, means that a collection or range of values that are included. For example, "about X" includes a range of values that are ±20%, ±10%, ±5%, ±2%, ±1%, ±0.5%, ±0.2%, or ±0.1% of X, where X is a numerical value. In one embodiment, the term "about" refers to a range of values which are 5% more or less than the specified value. In another embodiment, the term "about" refers to a range of values which are 2% more or less than the specified value. In another embodiment, the term "about" refers to a range of values which are 1% more or less than the specified value.

The use of the articles "a", "an", and "the" in both the following description and claims are to be construed to cover both the singular and the plural, unless otherwise indicated herein or clearly contradicted by context. The terms "comprising", "having", "being of" as in "being of a chemical formula", "including", and "containing" are to be construed as open terms (i.e., meaning "including but not limited to") unless otherwise noted. Additionally whenever "comprising" or another open-ended term is used in an embodiment, it is to be understood that the same embodiment can be more narrowly claimed using the intermediate term "consisting essentially of" or the closed term "consisting of."

As used herein, the phrases "for example," "for instance," "such as," or "including" are meant to introduce examples that further clarify more general subject matter. These examples are provided only as an aid for understanding the disclosure, and are not meant to be limiting in any fashion.

In one aspect, the present disclosure provides a method of treating a liver disorder or lipid disorder in a subject in need thereof, the method comprising: (a) administering a first dose of 2-(3,5-dichloro-4-((5-isopropyl-6-oxo-1,6-dihydropyridazin-3-yl)oxy)phenyl)-3,5-dioxo-2,3,4,5-tetrahydro-1,2,4-triazine-6-carbonitrile ("Compound A" or "MGL-3196") to the subject daily for a first period of time; (b) performing a test selected from the group consisting of a genetic test, a biomarker test, and a pharmacokinetic test on a biological sample obtained from the subject, a physical examination of the subject, and a combination thereof, to determine sensitivity of the subject to Compound A after step (a); and (c) administering a second dose of Compound A to the subject for a second period of time based on the sensitivity result from step (b). In one embodiment, the test of step (b) is a biomarker test measuring the expression level of at least one biomarker. In one embodiment, the method further comprises (d) performing a first biomarker test on a first biological sample obtained from the subject before step (a), wherein the first biomarker test measures the expression level of at least one biomarker that is to be measured in step (b); and (e) determining a change or degree of change in the expression level of the at least one biomarker based on the results in steps (b) and (d). In one embodiment, the method further comprises step (f) determining the second dose of Compound A based on the change or degree of change determined in step (e). The change can be either an increase or decrease of the expression level.

In one aspect, the present disclosure provides Compound A for use in a method of treating a liver disorder or lipid disorder in a subject in need thereof, the method comprising: (a) administering a first dose of Compound A to the subject daily for a first period of time; (b) performing a test selected from the group consisting of a genetic test, a biomarker test, and a pharmacokinetic test on a biological sample obtained from the subject, a physical examination of the subject, and a combination thereof, to determine sensitivity of the subject to Compound A after step (a); and (c) administering a second dose of Compound A to the subject for a second period of time based on the sensitivity result from step (b).

In one aspect, the present disclosure provides the use of Compound A in the manufacture of a medicament for use in a method of treating a liver disorder or lipid disorder in a subject in need thereof, the method comprising: (a) administering a first dose of Compound A to the subject daily for a first period of time; (b) performing a test selected from the group consisting of a genetic test, a biomarker test, and a pharmacokinetic test on a biological sample obtained from the subject, a physical examination of the subject, and a combination thereof, to determine sensitivity of the subject to Compound A after step (a); and (c) administering a second dose of Compound A to the subject for a second period of time based on the sensitivity result from step (b).

In one aspect, the present disclosure also provides a method of treating a liver disorder or lipid disorder in a subject in need thereof, the method comprising: (a) performing a test selected from the group consisting of a genetic test, a biomarker test, and a pharmacokinetic test on a biological sample obtained from the subject, a physical examination of the subject, and a combination thereof; (b) determining a therapeutically effective amount of Compound A for the subject based on the result of test; and (c) administering the therapeutically effective amount of Compound A to the subject. In one embodiment, a predictive algorithm is used in step (b) to determine the therapeutically effective amount of Compound A.

In one aspect, the present disclosure provides Compound A for use in a method of treating a liver disorder or lipid disorder in a subject in need thereof, the method comprising: (a) performing a test selected from the group consisting of a genetic test, a biomarker test, and a pharmacokinetic test on a biological sample obtained from the subject, a physical examination of the subject, and a combination thereof; and (b) determining a therapeutically effective amount of Compound A for the subject based on the result of the test.

In one aspect, the present disclosure provides the use of Compound A in the manufacture of a medicament for use in a method of treating a liver disorder or lipid disorder in a subject in need thereof, the method comprising: (a) performing a test selected from the group consisting of a genetic test, a biomarker test, and a pharmacokinetic test on a biological sample obtained from the subject, a physical examination of the subject, and a combination thereof; and (b) determining a therapeutically effective amount of Compound A for the subject based on the result of the test.

Compound A is a thyroid hormone receptor (THR)-beta agonist and has the following structure:

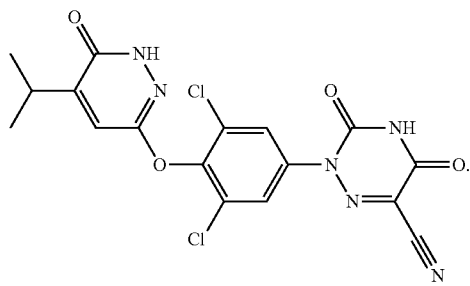 [SMILES: CC(C)c1cc(Oc2c(Cl)cc(-n3nc(C#N)c(=O)[nH]c3=O)cc2Cl)n[nH]c1=O]

In one embodiment, a single test (e.g., a genetic test, a biomarker test, a pharmacokinetic test, or a physical examination) can be performed for any of the methods disclosed herein. In one embodiment, a combination of two or more tests can be performed for any of the methods disclosed herein. For example, the test can include one or more genetic tests optionally combined with one or more physical examinations, one or more biomarker tests optionally combined with one or more physical examinations, one or more pharmacokinetic tests optionally combined with one or more physical examinations, one or more genetic tests optionally combined with one or more biomarker tests, one or more genetic tests optionally combined with one or more pharmacokinetic tests, or one or more biomarker tests optionally combined with one or more pharmacokinetic tests, or a combination of any three or four types of the tests (a genetic test, a biomarker test, a pharmacokinetic test, or a physical examination). In one embodiment, the physical examination includes measuring the body mass index (BMI). For example, patients within different BMI ranges may be administered with difference doses of Compound A. For example, patients having a BMI less than 45 kg/m$^2$ may be administered with a lower dose of Compound A as compared to those having a BMI greater than 45 kg/m$^2$. For example, patients having a BMI less than 45 kg/m$^2$ may be administered with a higher dose of Compound A as compared to those having a BMI greater than 45 kg/m$^2$. In one embodiment, a subject having a BMI of less than 45 kg/m$^2$ is administered Compound A at a dose of about 20 mg, 25 mg, 30 mg, 35 mg, 40 mg, 45 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, or 250 mg.

The test can have a specificity of at least 75%, at least 80%, at least 85%, at least 90%, at least 91%, at least 92%, at least 93%, at least 94%, at least 95%, at least 96%, at least 97%, at least 98%, or at least 99%.

The test can have a sensitivity of at least 75%, at least 80%, at least 85%, at least 90%, at least 91%, at least 92%, at least 93%, at least 94%, at least 95%, at least 96%, at least 97%, at least 98%, or at least 99%.

In one embodiment, the pharmacokinetic test comprises measuring a level of a metabolite of Compound A in the biological sample at a predetermined time after the administration of the first dose. The metabolite of Compound A can comprise a compound having the following structure:

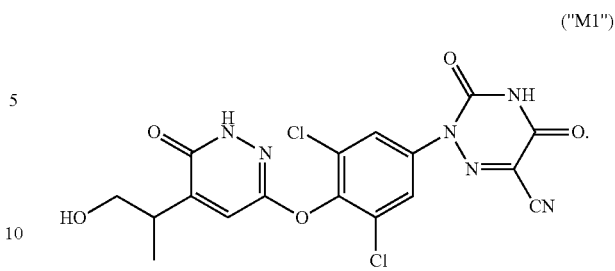

In one embodiments, the metabolite of Compound A can be a regioisomer of M1.

In one embodiment, the predetermined time can be at least 20 minutes, e.g., at least 40 minutes, at least 1 hour, at least 2 hours, at least 3 hours, or at least 6 hours. In one embodiment, the predetermined time can be in the range of 20 minutes to 12 hours, e.g., 20 minutes to 10 hours, 20 minutes to 8 hours, 20 minutes to 6 hours, 1 hour to 6 hours, or 2 hours to 6 hours.

In one embodiment, the metabolite has a geometric mean of maximum plasma concentration ($C_{max}$) of about 100 ng/mL to 1000 ng/mL, e.g., about 100 ng/mL to 900 ng/mL, about 100 ng/mL to 800 ng/mL, or about 150 ng/mL to 800 ng/mL.

In one embodiment, the liver disorder is non-alcoholic fatty liver disease (NAFLD). NAFLD refers to a wide spectrum of liver diseases ranging from simple fatty liver (steatosis), to non-alcoholic steatohepatitis (NASH), to cirrhosis. In one embodiment, the liver disorder is NASH. All of the stages of NAFLD have in common the accumulation of fat in the hepatocytes. In NASH, the fat accumulation is associated with varying degrees of inflammation (hepatitis) and scarring (fibrosis) of the liver. NAFLD and NASH occur in individuals who do not consume excessive amounts of alcohol. Yet, in many respects, the histological picture of an NAFLD biopsy is similar to what can be seen in liver disease caused by alcohol abuse. NAFLD and NASH are considered the primary fatty liver diseases. The secondary fatty liver diseases include those that occur in other types of liver disease. Thus, alcoholic liver disease (ALD) is the most frequent secondary fatty liver disease. Secondary fatty liver can also occur in chronic viral hepatitis C (HCV), chronic viral hepatitis B (HBV), chronic autoimmune hepatitis (AIH), and Wilson's disease.

The symptoms of NAFLD and NASH are usually not dramatic and tend to be non-specific (as can also be observed in other diseases). The symptoms are minimal in most patients, who may, however, experience occasional, vague right upper-quadrant abdominal pain. This pain characteristically is dull and aching, without a predictable pattern of occurrence. It is not an intense, sudden, and severe pain, as might occur with, for example, gallstones. The abdominal pain in NAFLD and NASH is thought to be due to the stretching of the liver covering (capsule) when the liver enlarges and/or when there is inflammation in the liver. In contrast to ALD, hepatitis B, or hepatitis C, symptoms of severe, acute liver failure (e.g., jaundice, intense fatigue, loss of appetite, nausea, vomiting, and confusion) are not observed in NAFLD or NASH. Obesity and related conditions (e.g., diabetes, hypertension) are frequent seen among those suffering from NAFLD or NASH, and the classic signs of insulin resistance often dominate the physical exam in NAFLD and NASH. Acanthosis nigricans, a dark pigmentation of the skin of the armpits and neck, can be a sign of insulin resistance and is frequently seen in children with NASH. When the liver is palpated, it usually feels normal. However, when very large amounts of fat accumulate in the liver, it can become quite large with a soft, rounded edge that can be easily felt by the doctor.

In addition to the symptoms described above, a diagnosis of NAFLD or NASH is made based on the following criteria: clinical and/or biochemical signs of insulin resistance; chronically elevated ALT; signs of fatty liver on ultrasound; exclusion of other causes of elevated ALT and fatty liver. Only a liver biopsy, however, can establish a definite diagnosis and determine the severity of NAFLD or NASH.

In one embodiment, the lipid disorder is selected from the group consisting of dyslipidemia, hyperlipidemia, hypertriglyceridemia, hypercholesterolemia, low HDL and high LDL. For example, the hypercholesterolemia is heterozygous familial hypercholesterolemia (HeFH) or homozygous familial hypercholesterolemia (HoFH).

In one embodiment, the genetic test used in the present disclosure comprises detecting polymorphism in a polynucleotide encoding a drug transporter, a drug metabolizing enzyme, or a thyroid axis hormone, a thyroid pathway gene, a lipid pathway gene, or a combination thereof. There are at least two drug transporter superfamilies: the solute carrier (SLC) transporters and the ATP-binding cassette (ABC) transporters. SLC transporters include SLC22A1 (also known as OCT1), SLC22A2 (also known as OCT2), SLC22A3 (also known as OCT3), SLC22A6 (also known as OAT1 or NKT), SLC22A8 (also known as OAT3 or ROCT), SLC22A11 (also known as OCT4), SLCO1B1 (also known as OATP1B1), SLCO1B3 (also known as OATP1B3), SLCO2B1 (also known as OATP2B1) and members of the SLC47 family (e.g., SLC47A1 (also known as MATE1) or SLC47A2 (also known as MATE2)). ABC transporters include ABCC1 (also known as MRP1), ABCC2 (also known as MRP2), ABCC3 (also known as MRP3), ABCC4 (also known as MRP4), ABCC5 (also known as MRP5), ABCG2 (also known as BCRP), and ABCB11 (also known as BSEP). Additional information about drug transporters can be found, e.g., at SK Nigam, Nat. Rev. Drug Discov. 2015, 14(1), 29-44, the contents of which are incorporated herein by reference. In some embodiments, the drug transporter can be found in the liver. For example, the drug transporter is concentrated in the liver. In some embodiments, the drug metabolizing enzyme is CYP2C8.

Polymorphism in a drug transporter can have an effect on the handling of drugs by the drug transporter. Coding or non-coding single-nucleotide polymorphisms (SNPs) that result in clinical phenotypes have been reported for SLC22A6 and SLC22A8. Examples of polymorphism for ABCG2 include C421A and Q141K. Examples of methods for detecting polymorphism include, but are not limited to, selective oligonucleotide hybridization, selective amplification, selective primer extension, selective ligation, single-base extension, selective termination of extension or invasive cleavage assay.

There are at least two types of drug-metabolizing enzymes: oxidative drug metabolizing enzymes and conjugative drug metabolizing enzymes. Oxidative drug metabolizing enzymes include cytochrome P450 (e.g., CYP2D6, CYP2C19, CYP2E1, or CYP2C9) and flavin monooxygenases (e.g., FMO1, FMO2, FMO3, FMO4, FMO5, or FMO6). Conjugative drug metabolizing enzymes include UDP glycosyltransferases (e.g., UGT1A1, UGT1A3, UGT1A4, UGT1A6, UGT1A9, UGT2B4, UGT2B7, UGT2B10, UGT2B11, or UGT2B15), glutathione transferases (e.g., GST A1-1, GST M1-1, or GST P1-1), sulfotransferases (e.g., SULT1A1, SULT1A2, SULT1A3, SULT1E and SULT2A1), and N-acetyl transferases (e.g., NAT1 or NAT2). Polymorphism in drug-metabolizing enzymes are known in the art, e.g., Pinto and Dolan, Current Drug Metabolism, 2011, 12, 487-497, the contents of which are incorporated herein by reference.

In one embodiment, the biomarker test used in the present disclosure comprises measuring the expression level of a biomarker selected from the group consisting of thyroid axis hormones, thyroxine-binding globulin (TBG), sex hormone-binding globulin (SHBG), and a lipid biomarker. In one embodiment, the biomarker test is a pharmacodynamics test. In one embodiment, the biomarker test can be used to measure the expression level of the metabolite of the biomarker. In another embodiment, the biomarker test can be used to measure the expression level of the biomarker and the metabolite thereof. In one embodiment, the result of the biomarker test provides a ratio of the expression levels of two biomarkers.

Thyroid axis hormones are also called hypothalamic pituitary thyroid (HPT) or HPT axis hormones. In one embodiment, thyroid axis hormones include triiodothyronine (free T3), reverse T3, total T3, free thyroxine (T4), total T4, thyrotropin (TSH), a thyrotropin-releasing hormone (TRH), and a combination thereof. Total T3 refers to both bound T3 and free T3. Total T4 refers to both bound T4 and free T4. For example, the thyroid axis hormones are free T3, free T4, and TSH. For example, the thyroid axis hormones are TSH, TRH, total T3, and total T4. In one embodiment, the biomarker test measures the expression levels of free T3, free T4, and TSH, respectively. In another embodiment, the biomarker test measures the expression levels of free T3, free T4, and TSH in combination. In another embodiment, the biomarker test measures the expression levels of free T3, free T4, TSH, TRH, total T3, and total T4, respectively. In yet another embodiment, the biomarker test measures the expression levels of TSH, TRH, total T3, and total T4 in combination.

The lipid biomarker can be total cholesterol, triglycerides, low-density lipoprotein cholesterol (LDL-C), high-density lipoprotein cholesterol (HDL-C), non-HDL-C, lipoprotein (a), apolipoprotein A1 (ApoA-1), apolipoprotein B (ApoB), or a combination thereof. For example, the ApoB/ApoA-1 ratio can be used in the methods described herein.

In one embodiment, the pharmacokinetic test can be done through a bioanalytical method or mass spectrometry. Bioanalytical methods can be used to construct a concentration-time profile. Chemical techniques are employed to measure the concentration of drugs in biological matrix, most often plasma. Proper bioanalytical methods should be selective and sensitive. For example, microscale thermophoresis can be used to quantify how the biological matrix/liquid affects the affinity of a drug to its target. Pharmacokinetics can also be studied using mass spectrometry. The most common instrumentation used in this application is LC-MS with a triple quadrupole mass spectrometer. Tandem mass spectrometry is usually employed for added specificity.

In certain embodiments of the disclosure, the subject in need thereof is being administered or has been administered another therapeutic agent different from Compound A (e.g., a lipid-lowering drug, a diabetes drug, an organic anion-transporting polypeptide (OATP) inhibitor, an ABCG2 inhibitor, a CYP2C8 inhibitor, a drug that alters the pH of the gastrointestinal tract, an antacid, or a bile acid sequestrant). The different therapeutic agent may have an effect on the metabolism or absorption of Compound A. The therapeutic agent and Compound A can be administered concurrently, sequentially, or in alternation. For example, the therapeutic agent and Compound A can be administered concurrently. For example, the therapeutic agent can be administered prior to the administration of Compound A. For example, the therapeutic agent can be administered after the administration of Compound A. For example, the therapeutic agent and Compound A are administered in alternation. For example, the administrations of the therapeutic agent and Compound A can be separated by a certain period of time, e.g., several hours.

In one embodiment, the therapeutic agent different from Compound A can be a lipid-lowering drug. For example, the lipid-lowering drug can be a statin, a fibrate, niacin, a bile acid sequestrant, ezetimibe, lomitapide, phytosterols, or orlistat. Examples of statins include, but are not limited to, atorvastatin, cerivastatin, fluvastatin, lovastatin, mevastatin, pitavastatin, pravastatin, rosuvastatin, and simvastatin.

In one embodiment, the therapeutic agent different from Compound A can be a diabetes drug. Examples of diabetes drugs include, but are not limited to: (a) an antioxidant such as vitamin E, vitamin C, an isoflavone, zinc, selenium, ebselen, a carotenoid; (b) an insulin or insulin analogue such as regular insulin, lente insulin, semilente insulin, ultralente insulin, NPH or humalog; (c) an α-adrenergic receptor antagonist such as prazosin, doxazocin, phenoxybenzamine, terazosin, phentolamine, rauwolscine, yohimine, tolazoline, tamsulosin, or terazosin; (d) a β-adrenergic receptor antagonist such as acebutolol, atenolol, betaxolol, bisoprolol, carteolol, esmolol, metoprolol, nadolol, penbutolol, pindolol, propanolol, timolol, dobutamine hydrochloride, alprenolol, bunolol, bupranolol, carazolol, epanolol, moloprolol, oxprenolol, pamatolol, talinolol, tiprenolol, tolamolol, or toliprolol; (e) a non-selective adrenergic receptor antagonist such as carvedilol or labetolol; (f) a first generation sulphonylurea such as tolazamide, tolubtuamide, chlorpropamide, acetohexamide; (g) a second generation sulphonylurea such as glyburide, glipizide, and glimepiride; (h) a biguanide agent such as is metformin; (i) a benzoic acid derivative such as replaglinide; (j) a α-glucosidase inhibitor such as acarbose and miglitol; (k) a thiazolidinedione such as rosiglitazone, pioglitazone, or troglitazone; (l) a phosphodiesterase inhibitor such as anagrelide, tadalfil, dipyridamole, dyphylline, vardenafil, cilostazol, milrinone, theophylline, or caffeine; (m) a cholineresterase antagonist such as donepezil, tacrine, edrophonium, demecarium, pyridostigmine, zanapezil, phospholine, metrifonate, neostigmine, or galathamine; (n) a glutathione increasing compound such as N-acetylcysteine, a cysteine ester, L-2-oxothiazolidine-4-carboxolate (OTC), gamma glutamylcysteine and its ethyl ester, glytathtione ethyl ester, glutathione isopropyl ester, lipoic acid, cysteine, methionine, or S-adenosylmethionine; and (o) GLP and glucagon like peptide analogues, such as exanitide, DAC: GLP-1(CJC-1131), Liraglutide, ZP10, BIM51077, LY315902, LY307161 (SR).

In one embodiment, the therapeutic agent different from Compound A can be an OATP inhibitor. Examples of OATP inhibitors include, but are not limited to, gemfibrozil or cyclosporine A.

In one embodiment, the therapeutic agent different from Compound A can be an ABCG2 inhibitor. Examples of ABCG2 inhibitors include, but are not limited to, afatinib, aripiprazole, axitinib, curcumin, cyclosporine, elacridar, erlotinib, fluvastatin, fumitremorgin C, gefitinib, ivermectin, ko143, lapatinib, nilotinib, novobiocin, pantoprazole, pitavastatin, ponatinib, quercetin, quizartinib, rabeprazole, regorafenib, rilpivirine, sulfasalazine, sunitinib, tacrolimus, teriflunomide, trametinib, trifluoperazine, and vismodegib.

In one embodiment, the therapeutic agent different from Compound A can be a CYP2C8 inhibitor. Examples of CYP2C8 inhibitors include, but are not limited to, gemfibrozil, clopidogrel, fluvoxamine, ketoconazole, fenofibrate, fenofibric acid, montelukast, nicardipine, quercetin, simvastatin, spironolactone, trimethoprim, and vilazodone.

In one embodiment, the therapeutic agent different from Compound A can be an antacid. Examples of antacids include, but are not limited to, aluminum carbonate, aluminum hydroxide, aluminum phosphate, aluminum hydroxycarbonate, dihydroxy aluminum sodium carbonate, aluminum magnesium glycinate, dihydroxy aluminum amino acetate, dihydroxy aluminum aminoacetic acid, calcium carbonate, calcium phosphate, aluminum magnesium hydrated sulfates, magnesium aluminate, magnesium alumino silicates, magnesium carbonate, magnesium glycinate, magnesium hydroxide, magnesium oxide, magnesium trisilicate, sucrafalte, and sodium bicarbonate.

In one embodiment, the therapeutic agent different from Compound A can be a bile acid sequestrant. Examples of antacids include, but are not limited to, cholestyramine, colestipol, and colesevelam.

In one embodiment, the subject is administered a statin and Compound A. The statin can be administered concurrently with Compound A. The statin can be administered prior to the administration of Compound A. The statin can be administered after the administration of Compound A. The administrations of the statin and Compound A can be separated by a certain period of time, e.g., about 1-24 hours, about 1-20 hours, about 1 to 16 hours, about 1-12 hours, about 6-12 hours. For example, the administrations of the statin and Compound A are separated by about 6 hours, about 7 hours, about 8 hours, about 9 hours, about 10 hours, about 11 hours, or about 12 hours. In one embodiment, the statin is administered in the evening and Compound A is administered in the morning on the next day.

In one embodiment, a first dose of Compound A is administered to a population of patients (e.g., daily) for a first period of time and the test is performed subsequently on these patients to determine their respective sensitivity levels to Compound A. For example, the sensitivity level can be determined based on a change or degree of change of the expression level of at least one of the biomarkers disclosed herein; or the sensitivity level can be determined based on a combination of the expression level change and the results of another type of test (e.g., a genetic test, a physical examination, or a combination thereof). The period of time can be in the range of about 2-21 days (e.g., 5 days, 7 days, 10 days, or 14 days). Based on the sensitivity levels, the patients can be divided into at least the following three sub-populations. A first sub-population consists of patients whose sensitivity levels to Compound A are normal or average. A second sub-population consists of patients whose sensitivity levels to Compound A is above the normal or average sensitivity level (e.g., at least 10%, at least 20%, at least 30%, at least 40%, at least 50%, at least 60%, at least 70%, at least 80%, or at least 90% above the normal or average sensitivity level). A third sub-population consists of patients whose sensitivity levels are below the normal or average sensitivity level (e.g., at least 10%, at least 20%, at least 30%, at least 40%, at least 50%, at least 60%, at least 70%, at least 80%, or at least 90% below the normal or average sensitivity level). These stratified patient sub-populations can be used as a reference for determining a therapeutically effective dose for individual patients.

In one embodiment, based on the result of a test described herein on an individual patient (whether with or without a prior treatment with Compound A), a person in a care-taking position such as a physician can determine which sub-population the individual patient belongs to and prescribe a therapeutically effective amount of Compound A in accordance with the determination. In one embodiment, based on the result of the test, a predictive algorithm is used to determine the therapeutically effective amount of Compound A. Additional information can be used for the determination, such as at least one demographic feature of the subject (e.g., race, ethnicity, age, or gender), medication history of the subject (e.g., whether or not the subject is administered or has been administered at least one other therapeutic agent), physical information of the subject (e.g., weight, height, blood pressure, or heart rate). For example, the effective amount can maintain the effectiveness of the drug in the individual patient while minimizing its side effects on the individual patient. For example, the effective amount for patients belonging to the second sub-population is lower than that for patients belonging to the first sub-population; and the effective amount for patients belonging to the third sub-population is higher than that for patients belonging to the first sub-population.

Depending on the test result on the individual patient, an effective amount of Compound A is in the range of about 5 to 300 mg, about 10 to 250 mg, about 20 to 200 mg, about 20 to 150 mg, about 20 to 100 mg, about 50 to 200 mg, or about 50 to 150 mg. An effective amount can be about 5 mg, 10 mg, 15 mg, 20 mg, 25 mg, 30 mg, 35 mg, 40 mg, 45 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, or 250 mg. For example, an effective amount of Compound A is in the range of about 5 to 300 mg, about 10 to 250 mg, about 20 to 200 mg, about 20 to 150 mg, about 20 to 100 mg, about 50 to 200 mg, or about 50 to 150 mg daily. An effective amount can be about 5 mg, 10 mg, 15 mg, 20 mg, 25 mg, 30 mg, 35 mg, 40 mg, 45 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, or 250 mg daily.

In another embodiment, a first dose of Compound A is administered to the subject daily for a first period of time and then a test (e.g., selected from the group consisting of a genetic test, a biomarker test, and a pharmacokinetic test on a biological sample obtained from the subject, a physical examination of the subject, and a combination thereof) is used to determine the subject's sensitivity level to Compound A. The first period of time can be in the range of about 2-21 days (e.g., about 5 days, about 7 days, about 10 days, or about 14 days). The sensitivity level permits a person in a care-taking position such as a physician to determine a second dose of Compound A for the subject for a second period of time. For example, when the subject's sensitivity level is above the average sensitivity level, the second dose is lower than the first dose; when the subject's sensitivity level is the same as that average sensitivity level, the second dose is the same as the first dose; and when the subject's sensitivity level is below the average sensitivity level, the second dose is higher than the first dose. The second period of time can last for as long as the subject needs the treatment. For example, the second period of time can be about 7 days to 365 days. In some embodiments, the second period of time can be about 1 month to 36 months, e.g., 3 months to 24 months.

For example, the first dose of Compound A can be a dose that is expected to have an effect on at least one of the biomarkers disclosed herein. In one embodiment, a multiple-dose study can be performed in a population of subjects who are divided into cohorts, where different doses of Compound A are administered to different cohorts of subjects and the expression level of at least one biomarker are monitored after the administration. For a cohort of subjects who are administered a particular dose of Compound A, a statistically significant change of the expression level of the at least one biomarker is an indication that the particular dose has an effect on the at least one biomarker. For example, a statistically significant change of the expression level of the at least one biomarker can be a statistically significant reduction in the level of T4 or LDL-cholesterol. More information regarding dose study of Compound A can be found, e.g., at Taub et al., Atherosclerosis, 2013, 373-380, the contents of which are incorporated herein by reference.

For example, the first dose of Compound A can be determined based on the patient stratification methods described herein. For example, the first dose of Compound A can be in the range of about 5 to 300 mg, about 10 to 250 mg, about 20 to 200 mg, about 20 to 150 mg, about 20 to 100 mg, about 50 to 200 mg, or about 50 to 150 mg. The first dose can be about 5 mg, 10 mg, 15 mg, 20 mg, 25 mg, 30 mg, 35 mg, 40 mg, 45 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, or 250 mg. In one embodiment, Compound A is administered once daily, twice daily, or three times daily.

For example, a first biomarker test is performed on a first biological sample obtained from the subject before the first dose of Compound A is administered to measure the expression level of at least one biomarker. A second biomarker test is performed on a second biological sample obtained from the subject after the first dose of Compound A has been administered for a first period of time to measure the expression level of the same biomarker. The first and second biological samples are of the same type. Based on the results of the first and second biomarker tests, one can determine whether or not there is a change and the degree of change in the expression levels of one or more biomarkers. The biomarkers can be of the same type or different types. For example, the biomarkers can include at least one thyroid axis hormone and at least one lipid biomarker; the biomarkers can include at least one thyroid axis hormone and sex hormone-binding globulin; the biomarkers can include at least one lipid biomarker and sex hormone-binding globulin; or the biomarkers can include at least one lipid biomarker, sex hormone-binding globulin, and at least one thyroid axis hormone. For example, the biomarkers can be LDL-C, ApoB, SHBG, T4, or a combination thereof. For example, depending on the subject's sensitivity to Compound A, the expression levels of one or more biomarkers can increase, decrease, or stay unchanged after the administration of the first dose of Compound A. The second dose is adjusted in accordance with the change in the expression levels. For example, an algorithm can be implemented to determine the second dose based on the change and the degree of change. In one embodiment, a genetic test, pharmacokinetic test, physical examination, or a combination thereof are performed in conjunction with the biomarker test to determine the second dose. For example, the physical examination can determine whether or not there is a change and a degree of change in the BMI of the subject, which can be a factor in adjusting the second dose. Additional information can be used for adjusting the second dose, such as at least one demographic feature of the subject (e.g., race, ethnicity, age, or gender), medication history of the subject (e.g., whether or not the subject is administered or has been administered at least one other therapeutic agent), physical information of the subject (e.g., weight, height, blood pressure, or heart rate). For example, the degree of change can be about 10%-500% as compared to the original tested data, e.g., 10%-400%, 10%-300%, 10%-200%, 10%-100%, 20%-200%, or 50%-100% as compared to the original tested data. For example, the degree of change can be about 10%, 20%, 30%, 40%, 50%, 60%, 70%, 80%, 90%, 100%, 110%, 120%, 130%, 140%, 150%, 160%, 170%, 180%, 190%, or 200% as compared to the original tested data.

For example, depending on the change and the degree of change, the second dose of Compound A can be lower or higher than the first dose. The second dose can also be the same as the first dose. For example, the second dose can be in the range of about 5 to 200 mg, about 10 to 200 mg, about 20 to 200 mg, about 20 to 150 mg, about 20 to 100 mg, about 50 to 200 mg, or about 50 to 150 mg. The second dose can be about 5 mg, 10 mg, 15 mg, 20 mg, 25 mg, 30 mg, 35 mg, 40 mg, 45 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, or 200 mg. In one embodiment, the second dose of Compound A is administered daily (e.g., once daily, twice daily, or three times daily), once every two days, twice weekly or once weekly.

In one embodiment, the test can further include an algorithm, e.g., for providing quantitative results based on the test. The algorithm can also be used in situations where the subject is being administered or has been administered another therapeutic agent different from Compound A (e.g., a lipid-lowering drug, a diabetes drug, an organic anion-transporting polypeptide (OATP) inhibitor, an ABCG2 inhibitor, a CYP2C8 inhibitor, a drug that alters the pH of the gastrointestinal tract, an antacid, or a bile acid sequestrant). Such therapeutic agent may play a role in determining the dose of Compound A for the subject (e.g., via its effect on the metabolism or absorption of Compound A). The algorithm can take into consideration the effect when determining a therapeutically effective amount of Compound A for the subject.

In one embodiment, the algorithm is a predictive algorithm, e.g., support vector machines (SVM), linear discriminant analysis (LDA), K-nearest neighbor (KNN) or naïve Bayes (NB). The algorithm can process the data produced in one or more tests to make a prediction regarding the subject's sensitivity to Compound A. For example, the data produced in the one or more tests can be the change or the degree of change of the expression levels of one or more biomarkers in response to the administration of a therapeutic agent to the subject. For example, the one or more biomarkers tested are selected from a thyroid axis hormone, thyroxine-binding globulin (TBG), sex hormone-binding globulin (SHBG), a lipid biomarker, and a combination thereof. The biomarkers can be of the same type or different types. For example, the biomarkers can include at least one thyroid axis hormone and at least one lipid biomarker; the biomarkers can include at least one thyroid axis hormone and SHBG; the biomarkers can include at least one lipid biomarker and SHBG; or the biomarkers can include at least one lipid biomarker, SHBG, and at least one thyroid axis hormone. For example, the biomarkers can be LDL-C, ApoB, SHBG, T4, or a combination thereof.

In vivo data have confirmed that Compound A exhibits interesting tissue uptake behavior. Specifically, the uptake of Compound A in the liver is high, while there is almost no uptake of Compound A in tissues outside the liver, such as the heart, bone/cartilage, or brain. Therefore, Compound A can be administered safely without the need for clinical monitoring. One aspect of the present disclosure relates to a method of treating a liver disorder or lipid disorder in a subject in need thereof, the method comprising administering an effective amount of Compound A daily to the subject, wherein the subject does not need clinical monitoring after the administration. In one embodiment, the effective amount is in the range of 5 to 300 mg (e.g., about 5 mg, about 20 mg, about 40 mg, about 50 mg, about 80 mg, about 100 mg, about 120 mg, about 140 mg, about 160 mg, about 180 mg, or about 200 mg). In one embodiment, the effective amount is in the range of 5 to 300 mg (e.g., (e.g., about 5 mg, about 20 mg, about 40 mg, about 50 mg, about 80 mg, about 100 mg, about 120 mg, about 140 mg, about 160 mg, about 180 mg, or about 200 mg) per day, e.g., via oral administration. In one embodiment, the clinical monitoring is selected from the group consisting of a bone scan, a heart scan, and a brain scan.

In one aspect, the present disclosure provides Compound A for use in treating a liver disorder or lipid disorder in a subject in need thereof, wherein the subject does not need clinical monitoring after the administration of Compound A.

In yet another aspect, the present disclosure provides the use of Compound A in the manufacture of a medicament for use in a method of treating a liver disorder or lipid disorder in a subject in need thereof, wherein the subject does not need clinical monitoring after the administration of the medicament.

Compound A can have a purity of greater than 85%, e.g., greater than 86%, greater than 90%, greater than 92.5%, greater than 95%, greater than 96%, greater than 97%, greater than 97.5%, greater than 98%, greater than 98.5%, greater than 99%, greater than 99.2%, greater than 99.5%, or greater than 99.8%.

All references to Compound A herein include all pharmaceutically acceptable salts and all solvates and alternative physical forms thereof unless otherwise stated. All doses recited herein for Compound A are based on the molecular weight of Compound A itself, rather than the pharmaceutically acceptable salt, hydrate of solvate thereof or any excipients in the composition, unless otherwise stated.

For therapeutic administration according to the present disclosure, Compound A may be employed in the form of its free base or in the form of a pharmaceutically acceptable salt.

In one embodiment, Compound A is crystalline, e.g., in a morphic form characterized by an X-ray powder diffraction pattern including peaks at about 10.5, 18.7, 22.9, 23.6, and 24.7 degrees 2θ (Form I). In one embodiment, Form I of Compound A has a purity of greater than 85%, e.g., greater than 86%, greater than 90%, greater than 92.5%, greater than 95%, greater than 96%, greater than 97%, greater than 97.5%, greater than 98%, greater than 98.5%, greater than 99%, greater than 99.2%, greater than 99.5%, or greater than 99.8%. More information about this specific morphic form is disclosed in U.S. Pat. No. 9,266,861, the contents of which are incorporated herein by reference in its entirety.

In one embodiment, Compound A is in a morphic form that is different from Form I. In certain embodiments, Compound A is in the form of a solvate, e.g., a hydrate (such as a dihydrate), dimethylacetamide (DMAC) solvate, or methyl isobutyl ketone (MIBK) solvate. See U.S. Pat. No. 9,266,861. The solvate has a purity of greater than 85%, e.g., greater than 86%, greater than 90%, greater than 92.5%, greater than 95%, greater than 96%, greater than 97%, greater than 97.5%, greater than 98%, greater than 98.5%, greater than 99%, greater than 99.2%, greater than 99.5%, or greater than 99.8%.

Compound A, or a pharmaceutically acceptable salt, prodrug, analog or derivative thereof, can be incorporated into pharmaceutical compositions suitable for administration. Such compositions typically comprise Compound A and a pharmaceutically acceptable excipient or carrier.

Pharmaceutically acceptable carriers include solid carriers such as lactose, terra alba, sucrose, talc, gelatin, agar, pectin, acacia, magnesium stearate, stearic acid and the like. Exemplary liquid carriers include syrup, peanut oil, olive oil, water and the like. Similarly, the carrier or diluent may include time-delay material known in the art, such as glyceryl monostearate or glyceryl distearate, alone or with a wax, ethylcellulose, hydroxypropylmethylcellulose, methylmethacrylate or the like. Other fillers, excipients, flavorants, and other additives such as are known in the art may also be included in a pharmaceutical composition according to this disclosure. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

In one embodiment, Compound A, or a pharmaceutically acceptable salt, prodrug, analog or derivative thereof, is administered in a suitable dosage form prepared by combining a therapeutically effective amount of Compound A, or a pharmaceutically acceptable salt, prodrug, analog or derivative thereof, (as an active ingredient) with standard pharmaceutical carriers or diluents according to conventional procedures (i.e., by producing a pharmaceutical composition of the disclosure). These procedures may involve mixing, granulating, and compressing or dissolving the ingredients as appropriate to attain the desired preparation.

A pharmaceutical composition of the disclosure is formulated to be compatible with its intended route of administration. Examples of routes of administration include parenteral, e.g., intravenous, intradermal, subcutaneous, oral, inhalation, transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic Compound A or a pharmaceutical composition of the disclosure can be administered to a subject in many of the well-known methods. For example, the dose chosen should be sufficient to constitute effective treatment but not so high as to cause unacceptable side effects. The state of the disease condition and the health of the patient should preferably be closely monitored during and for a reasonable period after treatment.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy.

The pharmaceutical compositions containing Compound A of the present disclosure may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one embodiment, the active compounds are prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved.

Compound A or the pharmaceutical compositions thereof can be included in a container, pack, or dispenser together with instructions for administration.

Compound A or the pharmaceutical compositions thereof can be administered once a day, twice a day, three times a day, once every other day, or once a week.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not to the remainder of the text of this application, in particular the claims of this application.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed invention. Based on the present disclosure the skilled artisan can identify and employ other components and methodology useful for practicing the present disclosure.

EXAMPLES

Example 1

Excretion Mass Balance, Pharmacokinetics, and Tissue Distribution by Quantitative Whole-Body Autoradiography in Rats Following a Single Oral Administration of [$^{14}$C]MGL-3196 (Compound A)

The study utilized 2 groups of male SD rats (Groups 1 and 2) and 1 group of male LE rats (Group 3); which were obtained from Hilltop Lab Animals, Inc. (Scottdale, Pa.). Group 1 was used for evaluation of excretion mass balance; Group 2 was used for evaluation of plasma total radioactivity PK; and Group 3 was used for evaluation of tissue distribution of total radioactivity. All rats received a single PO dose of [$^{14}$C]MGL-3196. The target dose was 5 mg/kg using a formulation prepared in a 4% DMSO/96% of 2% Klucel, 0.1% Tween-80, 0.09% methylparaben and 0.01% propylparaben in purified MilliQ water vehicle.

The primary route of elimination of radioactivity after a single PO dose of [$^{14}$C]MGL-3196 in Group 1 rats was in the feces, which accounted for a mean of 68.6% of the administered dose. An average of 16.2% of the administered dose was recovered in the urine. An average of 1.3% of the administered dose was recovered in the cage residues and an average of 1.1% of the administered dose was recovered in the carcass. The average total recovery of radioactivity in Group 1 rats was 87.2% of the administered dose.

Excretion data indicated that after a single PO dose, the majority of the [$^{14}$C]MGL-3196-derived radioactivity was recovered after 72 h in the feces in male SD rats.

The mean $C_{max}$ of plasma total radioactivity after a single PO dose of [$^{14}$C]MGL-3196 in Group 2 was 2230 ng equiv/mL at 4 h post-dose ($T_{max}$). Mean plasma radioactivity concentrations decreased over time with a $t_{1/2}$ of 9.6 h. The mean $AUC_{inf\ obs}$ of plasma total radioactivity was 25346 ng equiv·h/mL.

The $C_{max}$ of blood total radioactivity (by LSC) after a single PO dose of [$^{14}$C]MGL-3196 in Group 3 LE males was 645 ng equiv/g at 8 h post-dose ($T_{max}$). Blood radioactivity concentrations decreased slowly over time with a $t_{1/2}$ of 447.6 h. The $AUC_{inf\ obs}$ of blood total radioactivity was 54361 ng equiv·h/g. The $C_{max}$ of plasma total radioactivity (by LSC) after a single PO dose of [$^{14}$C]MGL-3196 in Group 3 LE males was 1078 ng equiv/mL at 4 h post-dose ($T_{max}$). Plasma radioactivity concentrations decreased slowly over time with a $t_{1/2}$ of 54.6 h. The $AUC_{inf\ obs}$ of plasma total radioactivity was 20430 ng equiv·h/mL.

Blood-to-plasma radioactivity concentration ratios ranged from 0.57 to 0.98 through 24 h post-dose, and from 1.52 to 5.62 from 48-168 h post-dose.

Drug-derived radioactivity was rapidly absorbed and widely distributed throughout the body of male LE rats, with quantifiable concentrations present in many tissues through 768 h (17 of 40 tissues).

In general, concentrations in most tissues of pigmented rats were lower than or similar to those in blood (cardiac). $C_{max}$ in most tissues (34 of 40) were observed at 8 h post-dose ($T_{max}$). Tissue concentrations >700 ng equiv/g at $C_{max}$ were found in the following tissues: liver, kidney cortex, cecum, urinary bladder, kidney medulla, small intestine, esophagus, cardiac blood, pigmented skin, and non-pigmented skin. Tissue concentrations that were <100 ng equiv/g at $C_{max}$ were observed in brain (medulla, cerebellum, cerebrum), eye lens, spinal cord, and bone. Radioactivity concentrations observed at 1392 h post-dose, which were >7.90 ng equiv/g, were present in 7 of 40 tissues (blood, liver, Harderian gland, pancreas, pigmented skin, lung, eye lens), but all tissues were approaching the lower limit of quantitation of radioactivity, which suggested that elimination was nearly complete.

Tissue to plasma ratios determined for all tissues up to 8 h post-dose (i.e., the distribution phase), which are indicative of tissue penetration, suggested that [$^{14}$C]MGL-3196-derived radioactivity highly penetrated liver, kidney, and cecum at multiples much higher than can be explained by the presence of radioactivity in the organ's blood vasculature. The ratios for all tissues, except liver, kidney, urinary bladder, and cecum, were <1, throughout the distribution phase, which suggested much lower penetration into most other tissues. Together, the data suggest that MGL-3196 was more specifically taken up by the liver, kidney, and cecum.

The highest concentrations of radioactivity in male LE rats were found in non-tissues in alimentary canal contents, bile, and urinary bladder contents.

Tissue concentration versus time profiles for male LE rats showed that most tissues had a slow elimination/tissue release phase that occurred from 24 to 768 h. Tissues with the longest reliable half-life ($t_{1/2}$) values (>400.0 h) were: Harderian gland, lung, pancreas, cardiac blood, skeletal muscle, bone marrow, and stomach. Reliable $t_{1/2}$ values were determined for 21 of 40 tissues. The $t_{1/2}$ for the concentration-time curves of remaining tissues could not be determined due to insufficient time point data, and/or resulting $r^2$ values that were <0.85.

The primary route of elimination of radioactivity in intact SD rats (Group 1) after a PO dose of [$^{14}$C]MGL-3196 was in the feces (68.6%), and less was recovered in the urine (16.2%). An average total of 87.2% of the dose was recovered through 168 h.

[$^{14}$C]MGL-3196-derived radioactivity was quantifiable in plasma of male SD rats through 48 h (the last time point for this group). The $C_{max}$ of total radioactivity in plasma was 2230 ng equiv/mL, which was observed at 4 h. The $t_{1/2}$ of mean plasma total radioactivity in SD rats was 9.6 h. The mean $AUC_{inf\,obs}$ of plasma total radioactivity in SD rats was 25346 ng equiv·h/mL.

[$^{14}$C]MGL-3196-derived radioactivity was quantifiable in blood of male LE rats through 768 h. The $t_{1/2}$ of blood total radioactivity in LE rats was 447.6 h. The $AUC_{inf\,obs}$ of blood total radioactivity in LE rats was 54361 ng equiv·h/g. [$^{14}$C]MGL-3196-derived radioactivity was quantifiable in plasma of male LE rats through 168 h, and the $t_{1/2}$ was 54.6 h. The longer $t_{1/2}$ value obtained for Group 3 rats is believed to be due to the inclusion of low plasma concentrations at later time-points from tissue release. The $AUC_{inf\,obs}$ of plasma total radioactivity in LE rats was 20430 ng equiv·h/mL, which was similar to that observed in SD rats in Group 2.

Blood-to-plasma radioactivity concentration ratios ranged from 0.57 to 0.98 through 24 h, which suggested that most of the radioactivity in blood was in the plasma fraction. Blood-to-plasma ratios ranged from 1.52 to 5.62 from 48-168 h post-dose, which suggested that most of the radioactivity was partitioned into the cellular portion of blood at later time-points.

[$^{14}$C]MGL-3196-derived radioactivity was widely distributed throughout the body of pigmented male rats after a single PO dose. Liver AUC of [$^{14}$C]MGL-3196 was approximately 10× higher than plasma, and kidney cortex AUC was approximately 3× higher than plasma, whereas skeletal and heart muscle, and most other tissues were lower or similar to the AUC in plasma and blood (blood was about 2× higher than plasma). The liver:plasma $AUC_{all}$ ratio was 10.5, and the volume fraction of plasma in the liver is approximately 0.06-0.14 (i.e., half of the volume fraction of blood in liver). Together, these data suggested selective uptake of MGL-3196 into liver and kidney cortex, and that concentrations in other tissues were mostly due to concentrations present in plasma and/or blood in the vasculature of remaining tissues.

Example 2

Liver Uptake and Preclinical ADME of Compound A

The following studies have been conducted: (a) in vitro drug protein binding, transporter (organic anion transporting polypeptide [OATP], P-glycoprotein [P-gp], breast cancer-related protein [BCRP], and multiple drug resistance protein 1 [MDR1]), and cytochrome P-450 enzyme assays to investigate absorption, distribution, and excretion; (b) in vivo MGL-3196 rat and dog oral PK and bioavailability studies; (c) in vivo $^{14}$C-MGL-3196 rat and dog oral pharmacokinetics, absorption, excretion, and tissue distribution by quantitative whole-body autoradiography (QWBA) studies; and (d) liver disposition of MGL-3196 using an in vitro sandwiched hepatocyte model system (B-CLEAR® technology) in dog (SCDH) and human (SCHH) hepatocytes. Tables 1A-1B show $^{14}$C-MGL-3196 rat ADME study design.

TABLE 1A

| Group Number | Study | Strain | Dose Route | N, Gender | Target Dose Level (mg/kg) | Target Radioactivity Level (µCi/kg) | Target Dose Volume (mL/kg) | Target Dose Conc. (mg/mL) |
|---|---|---|---|---|---|---|---|---|
| 1 | Mass Balance | SD | PO | 3 M | 5 | ~200 | 5 | 1 |
| 2 | Plasma PK | SD | PO | 6 M | 5 | ~200 | 5 | 1 |
| 3 | QWBA | LE | PO | 9 M (+2 M) | 5 | ~200 | 5 | 1 |

TABLE 1B

| Group Number | Urine | Feces | Blood & Plasma | Carcass | Cage Rinse, Wash & Wipe |
|---|---|---|---|---|---|
| 1 (MB) | Pre-dose, 0-8, 8-24, 24-h intervals to 168 h | Pre-dose, 24-h intervals to 168 h | N/A | 168 h | 24-h intervals to 168 h |
| 2 (PK) | N/A | N/A | Plasma samples from 3 rats/time-point (2 subgroups) at pre-dose, 1, 2, 4, 6, 8, 12, 24 and 48 h | N/A | N/A |
| 3 (QWBA) | N/A | N/A | 1, 2, 4, 8, 24, 48, 72, 96, and 168 h post-dose; plus 2 "TBD" rats to be dosed, but analyzed only if requested. N = 1/time-point | 1, 2, 4, 8, 24, 48, 72, 96, and 168 h post-dose: plus 2 "TBD" rats to be dosed, but analyzed only if requested. N = 1/time-point | N/A |

Tables 2A-2B show $^{14}$C-MGL-3196 dog ADME study design.

TABLE 2A

| Treatment | Study | Route | No. of Animals/ Sex | Dose Level (mg/kg) | $^{14}$C Dose Level (µCi/kg) | Dosing Regimen |
|---|---|---|---|---|---|---|
| 1 | Mass balance | PO | 3M | 100 | 100 | 3 days of dosing with MGL-3196 followed by a last dose of $^{14}$C-MGL-3196 on day 4 |
| 2 | Liver Bile, Plasma Distribution | PO | 3M | 100 | 100 | 3 days of dosing with MGL-3196 followed by a last dose of $^{14}$C-MGL-3196 on day 4 |

TABLE 2B

| Group Number | Urine | Feces | Blood & Plasma | Tissues | Cage Rinse, Wash & Wipe |
|---|---|---|---|---|---|
| 1 (MB) | Pre-dose, 0-8, 8-24, 24-h intervals to 168 h | Pre-dose, and @ 24-h intervals to 168 h | Plasma samples from each dog @, pre-dose 1, 2, 4, 6, 8, 12, 24, and 48 h | | 24-h intervals to 168 h |
| 2 (Tissue & plasma assays) | N/A | N/A | Plasma samples (systemic and from hepatic portal vein) from each dog @ 4 h | Liver, Plasma, Bile, Bile duct samples from each dog @ 4 h | N/A |

Qualyst Transporter Solutions evaluated the hepatic uptake of MGL-3196 in sandwich cultured human hypetocytes (SCHH). MGL-3196 was evaluated at 30 µM after a 20-minute incubation (based on a pilot uptake study) in the presence of a physiologic concentration of bovine serum albumin (BSA, ~4%). The experiment was performed in a 24-well format using 1 lot of Transporter Certified™ human hepatocytes (N=1). Each test condition was performed in 3 wells to provide triplicate data. Sample preparation and LC/MS/MS analysis of cell lysate to determine concentrations of MGL-3196 was performed at QTS according to analytical assay methodology and analytical standards supplied by Madrigal Pharmaceuticals. The following parameter for test article were determined: (a) total accumulation (hepatic uptake), (b) cellular accumulation (intracellular concentration), (c) biliary excretion index (hepatic efflux), (d) Kp value (hepatic accumulation), (e) in vitro biliary clearance (predictive of in vivo biliary clearance), and (f) media accumulation (post incubation supernatant).

Parameters determined:

Bile Accumulation=Total Accumulation$_{plus(+)Buffer}$−Cellular Accumulation$_{Minus(-)Buffer}$ $$\text{Biliary Excretion index} = 100 \times \frac{BileAccumulation}{TotalAccumulation_{Plus(+)Buffer}}$$

AUC=(Incubation Time)*(Analyte Concentration$_{Media}$)

In vitro biliary clearance:

$$Cl_{biliary} = \frac{BileAccumulation}{AUC} * ScalingFactor\left(\text{i.e., } mg\frac{protein}{kg}BW\right)$$

$$K_P = \frac{ICC}{AnalyteConcentration_{Total}}$$

($K_p$ ratio reflects the extent of MGL-3196 accumulation in hepatocyte to the total MGL-3196 concentration in the buffer, outside of the hepatocyte).

Plasma Protein Binding of MGL-3196 is >99% for all species.

In vitro drug transporter & Cytochrome P-450 Enzyme Assays are shown in Table 3.

TABLE 3

| Compound | Substrate for: | Inhibitor of: |
|---|---|---|
| MGL-3196 | CYP2C8; CYP2C9; OATP1B1; OATP1B3; BCRP BSEP MDR1 (P-gp) (weak) | CYP2C8 ($IC_{50}$ = 0.9 uM) CYP2C9 ($IC_{50}$ = 22 uM) CYP3A4 (weak inhibitor) OAT3 ($IC_{50}$ = 4.5 uM) OATP1B1 ($IC_{50}$ = 3.7 uM; 29% @ 10 uM Pravastatin) OATP1B3 (57% @ 10 uM Pravastatin) BCRP ($IC_{50}$ = 27.4 uM for Estrone-3-sulfate; 24% @ 25 uM genistein) BSEP (weak; inhibited BSEP-mediated transport of TCA with an $IC_{50}$ value of 34.7 µM) |
| MGL-3623 (M1) from CYP2C8 | CYP 2C8 OATP1B1 OATP1B3 | CYP2C8 ($IC_{50}$ = 6.1 uM); CYP2B6, CYP2C9, CYP2C19 weak ($IC_{50}$ = 24-35 µM) CYP3A4/5 weak ($IC_{50}$ = 35 uM) CYP1A2 & CYP2D6 ($IC_{50}$ > 50 uM) OATP1B1 insignificant (23% inhib @10 uM) OATP1B3 weak ($IC_{50}$ = 22.6 uM) |

MGL-3196 is a weak substrate for MDR1 and not a substrate MRP2. MGL-3196 is not an inhibitor: MDR1, MRP2, OCT2, CYP2C19, CYP1A2, CYP2A6, CYP2B6, CYP2D6, and CYP3A4/5.

Rat & Dog PK/Bioavailability Studies were also performed. MGL-3196 reached maximum plasma concentrations in rats and dogs after oral dosing at 2-6 h and 1-8 h and mean elimination half-life=2.5-7 and 3-5.5 h, respectively. Mean bioavailability ranged from 45-98%, and 11-135% in the rat, and dog, respectively.

Rat $^{14}$C-MGL-3196 Absorption, Distribution, Excretion was studied. MGL-3196 highly penetrates liver, has high concentrations in bile, is eliminated in gut, and less uptake in kidney and renal elimination. Liver exposure of $^{14}$C-MGL-3196 was on average ~10× higher than plasma. Penetration of MGL-3196 into other tissues including brain, heart, and bone was low and could be explained by blood flow. Tables 4-6 show the pertinent results.

TABLE 4

| | Percent Recovery (Totals up to 168 h) | | | | |
|---|---|---|---|---|---|
| Sample | Rat#1 | Rat#2 | Ra#3 | Mean | SD |
| Urine | 16.9 | 17.6 | 14.1 | 16.2 | 1.8 |
| Feces | 62.9 | 71.6 | 71.3 | 68.6 | 4.9 |
| Residues | 1.7 | 1.3 | 0.9 | 1.3 | 0.4 |
| Carcass | 1.1 | 1.2 | 1.0 | 1.1 | 0.1 |
| Total | 82.6 | 91.7 | 87.3 | 87.2 | 4.5 |

TABLE 5

| | Tissue to Plasma Ratios | | | | |
|---|---|---|---|---|---|
| Sample | $C_{max}$ | 1 h | 2 h | 4 h | 8 h |
| Plasma | 1.00 | 1.00 | 1.00 | 1.00 | 1.00 |
| Adrenal Gland | 0.51 | 0.34 | 0.35 | 0.28 | 0.56 |
| Brain | 0.08 | ND | ND | 0.03 | 0.09 |
| Heart | 0.57 | 0.30 | 0.26 | 0.29 | 0.62 |
| Kidney | 2.97 | 3.51 | 2.28 | 2.97 | 2.98 |
| Liver | 12.76 | 16.28 | 12.40 | 12.76 | 11.90 |

TABLE 6

| | Tissue to Plasma Ratios | | | | |
|---|---|---|---|---|---|
| Sample | $C_{max}$ | 1 h | 2 h | 4 h | 8 h |
| Plasma | 1.00 | 1.00 | 1.00 | 1.00 | 1.00 |
| Lung | 0.62 | 0.41 | 0.42 | 0.48 | 0.68 |
| Muscle | 0.21 | 0.12 | 0.07 | 0.07 | 0.23 |
| Skin | 0.65 | 0.21 | 0.23 | 0.30 | 0.72 |
| Spleen | 0.33 | 0.17 | 0.10 | 0.13 | 0.36 |
| Thyroid | 0.42 | 0.27 | 0.45 | 0.20 | 0.46 |

Dog $^{14}$C-MGL-3196 Absorption, Distribution, Excretion was studied. A dog 14C-MGL-3196 mass balance study (100 mg/kg) showed that, of the radioactivity recovered, at least 92% was in feces, 2.7% in urine (~83% of total administered was recovered in feces and 2.5% in urine). At 4 h post-dose high levels of MGL-3196 were present in liver and bile, and the concentration in bile was ~80× and ~250× higher than in liver and plasma, respectively. The liver to plasma ratios at 4 and 24 h, (100 mg/kg) were 3.1 and 267 fold higher, respectively, indicating that the clearance from plasma is more rapid than clearance from liver. Tables 7 and 8 show the pertinent results.

TABLE 7

Mean ± SD Recovery of $^{14}$C-MGL-3196 Radioactivity from 3 Male Beagle Dogs Administered a Single Oral Dose of $^{14}$C-MGL-3196

| Parameter | Recovery |
|---|---|
| % of Dose in Urine[a] | 2.57 ± 1.296 (50.4) |
| % of Dose in Feces[a] | 76.3 ± 25.62 (33.6) |
| % of Dose in Cage Residue[a] | 4.55 ± 3.399 (74.8) |
| Total % of Dose Recovered[a,b] | 83.37 ± 24.063 (28.9) |

[a]0-168 hr post-dose
[b]Total = urine + feces + cage residue
Mean ± Standard Deviation (% RSD); N = 3

TABLE 8

Concentrations of MGL-3196 in Dog Plasma (ng/mL), Hepatic Portal Vein Plasma (ng/mL), Bile, (ng/mL) and Liver (ng/g) at 4 Hours Following Single Daily 100 mg/kg Oral Doses of MGL-3196 for Four Days

| Matrix | Dog 1 | Dog 2 | Dog 3 | Mean | SD |
|---|---|---|---|---|---|
| Systemic Plasma | 16,700 | 81,500 | 115,000 | 71,070 | 50,000 |
| Hepatic Portal Vein Plasma | 18,800 | 86,600 | 98,600 | 68,000 | 43,030 |
| Bile | 26,400,000 | 10,400,000 | 15,500,000 | 17,400,000 | 8,170,000 |
| Liver | 129,000 | 319,000 | 210,000 | 219,000 | 95,300 |

Liver Disposition of MGL-3196 Using In Vitro sandwiched Dog and Human Hepatocyte Model Systems was studied. The data suggested that MGL-3196 accumulated in human and dog hepatocytes through active uptake and was excreted into bile. Tables 9 and 10 show the pertinent results.

TABLE 9

Hepatobiliary Disposition of MGL-3196 & M1 Following 20 min Exposure in SCHH

| Test Article | Conc. (µM) | Total Acc. pmol/mg | Std. Dev. | Cellular Acc. pmol/mg | Std. Dev. | Bile Acc. pmol/mg | Std. Dev. | BEI % | Std. Dev. | Cl$_{Biliary}$ mL/min/kg | Std. Dev. | ICC µM | Std. Dev. | Kp Ratio | Std. Dev. | PIS* µM | Std. Dev. |
|---|---|---|---|---|---|---|---|---|---|---|---|---|---|---|---|---|---|
| MGL-3196 | 30 | 863 5.79 | 39 0.46 | 570 4.01 | 34 0.049 | 293 1.78 | 69 0.47 | 33.7 30.4 | 6.7 5.7 | 1.45 | 0.34 | 74.2 0.521 | 4.4 0.0063 | 2.47 | 0.15 | BLQ | ND |

TABLE 10

Hepatobiliary Disposition of MGL-3196 & M1 Following 20 min Exposure in SCDH

| Test Article | Conc. (µM) | Total Acc. pmol/mg | Std. Dev. | Cellular Acc. pmol/mg | Std. Dev. | Bile Acc. pmol/mg | Std. Dev. | BEI % | Std. Dev. | Cl$_{Biliary}$ mL/min/kg | Std. Dev. | ICC+ µM | Std. Dev. | Kp Ratio | Std. Dev. | PIS* µM | Std. Dev. |
|---|---|---|---|---|---|---|---|---|---|---|---|---|---|---|---|---|---|
| MGL-3196 | 30 | 167 | 51 | 80.3 | 4.7 | 86.2 | 47 | 48.7 | 15 | 0.784 | 0.43 | 10.4 | 0.61 | 0.348 | 0.020 | BLQ | ND |
|  |  | BLQ | ND | BLQ | ND | ND | NA | ND | NA |  |  | ND | NA |  |  |  |  |
| d8-TCA | 5 | 9.12 | 2.1 | 5.22 | 1.9 | 3.90 | 1.4 | 43.4 | 14 | 0.43 | 0.15 | 0.68 | 0.24 | 0.14 | 0.05 |  |  |

MGL-3196 and its metabolite, MGL-3196-M1 (M1), were evaluated in sandwich-cultured human hepatocytes (SCHH) to evaluate the effects of temperature and concentration on total accumulation. Incubations were performed in presence of 4% bovine serum albumin (BSA) for 20 minutes at 37° C. and 4° C. across multiple concentrations (3, 10, 30, and 100 µM). Following the hepatic accumulation study, a species comparison of the hepatobiliary disposition of MGL-3196 (30 µM) and its metabolite, M1, was evaluated in SCHH and sandwich-cultured dog hepatocytes (SCDH) in the presence of 4% BSA.

Total accumulation (hepatocytes+bile) of MGL-3196 was demonstrated to be temperature-dependent, which suggested that MGL-3196 accumulation (≥72.8%) was mediated by an active uptake process in SCHH. Accumulation of M1 was reduced ≥65% in 4° C. incubations in SCHH across all MGL-3196 exposure levels examined. These results suggested that accumulation/formation of M1 was temperature-dependent, which was consistent with a metabolism-dependent mechanism.

A species comparison of the hepatobiliary disposition of MGL-3196 was performed in SCHH and SCDH. Total accumulation is reflective of hepatic accumulation potential of the test article. Total accumulation of MGL-3196 (30 µM) in SCDH was ~81% lower than accumulation observed in SCHH following a 20-minute exposure. Accumulation of M1 was below limits of detection (BLQ) in SCDH, but accumulation of M1 (0.67% of parent's total accumulation) was observed in SCHH. M1 was BLQ in cell culture media following 20 minutes of exposure to MGL-3196 (30 µM) in both species.

Biliary Excretion Index (BEI) describes the movement of molecules from inside the hepatocyte to the bile pocket quantifying the biliary efflux potential of a test article. The BEI (%) of MGL-3196 was greater in SCDH (48.7%) than SCHH (33.7%). In comparison, the BEI of d8-TCA, a model bile acid extensively excreted into bile, typically ranges from 30-50% and 50-75% in SCDH and SCHH, respectively.

In summary, these results suggested that MGL-3196 accumulation was mediated by an active uptake process in hepatocytes. Accumulation/formation of M1 was observed in SCHH only and was temperature-dependent consistent with a metabolism-dependent mechanism. M1 was BLQ in cell culture media following 20 minutes of exposure to MGL-3196 (30 µM) in both species. MGL-3196 biliary excretion was slightly greater in dog than human hepatocytes. However, biliary clearance estimates of MGL-3196 were ~46% lower in dog than human hepatocytes. The lower biliary clearance resulted from the markedly lower uptake (81% lower total accumulation) of MGL-3196 observed in SCDH. Overall, these results suggested that MGL-3196 has the potential to be eliminated in the bile of both species examined.

Human in vitro and animal in vivo analyses after dosing demonstrate that MGL-3196 is actively taken up into the liver and eliminated through bile. Distribution studies in rats and dogs showed that MGL-3196 localizes to the liver, and there is little to no penetration into other tissues.

What is claimed is:

1. A method of treating nonalcoholic steatohepatitis in a subject in need thereof, the method comprising:
   (a) performing a first biomarker test on a first biological sample obtained from the subject, wherein the first biomarker test measures a first expression level of a biomarker, the biomarker being sex hormone-binding globulin (SHBG);
   (b) administering a first dose of 2-(3,5-dichloro-4-((5-isopropyl-6-oxo-1,6-dihydropyridazin-3-yl)oxy)phenyl)-3,5-dioxo-2,3,4,5-tetrahydro-1,2,4-triazine-6-carbonitrile ("Compound A") to the subject daily for a first period of time;
   (c) performing a second biomarker test on a second biological sample obtained from the subject, wherein the second biomarker test measures a second expression level of SHBG;
   (d) determining a change or degree of change in the expression level of SHBG based on the results in steps (a) and (c), wherein the change or degree of change is indicative of the subject's sensitivity to Compound A; and
   (e) administering a second dose of Compound A to the subject for a second period of time based on the sensitivity result from step (d).

2. The method of claim 1, wherein the second dose of Compound A is further determined based on at least one demographic feature of the subject, medication history of the subject, physical information of the subject, a genetic test or a pharmacokinetic test on a biological sample obtained from the subject, a physical examination on the subject, or a combination thereof.

3. The method of claim 1, wherein the biological sample is a blood or serum sample.

4. The method of claim 1, wherein the first dose is in the range of about 5 to 300 mg.

5. The method of claim 1, wherein the second dose is in the range of about 5 to 300 mg.

6. The method of claim 1, wherein Compound A is in a morphic form characterized by an X-ray powder diffraction pattern including peaks at about 10.5, 18.7, 22.9, 23.6, and 24.7 degrees 2θ.

7. The method of claim 1, wherein the first period of time is in the range of about 2-21 days.

8. The method of claim 1, wherein Compound A is administered orally.

9. The method of claim 2, wherein the pharmacokinetic test comprises measuring a level of a metabolite of Compound A in the biological sample at a predetermined time after the administration of the first dose.

10. The method of claim 9, wherein the metabolite of Compound A comprises M1 having the following structure:

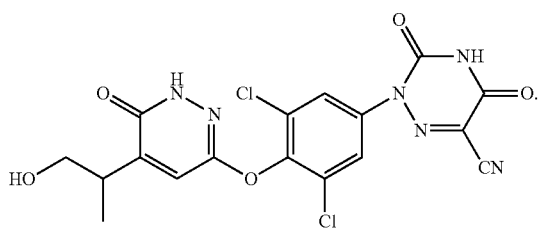 [SMILES: CC(CO)c1cc(Oc2c(Cl)cc(-n3nc(C#N)c(=O)[nH]c3=O)cc2Cl)n[nH]c1=O]

11. The method of claim 9, wherein the predetermined time is at least 20 minutes.

* * * * *